(12) United States Patent
Phadte et al.

(10) Patent No.: US 9,487,502 B2
(45) Date of Patent: Nov. 8, 2016

(54) CHEMICAL COMPOUNDS

(71) Applicants: Syngenta Limited, Guildford (GB); Syngenta Participations AG, Basel (CH)

(72) Inventors: Mangala Phadte, Ilhas (IN); Ravindra Sonaware, Ilhas (IN); James Alan Morris, Bracknell (GB); Alan Joseph Hennessy, Bracknell (GB); Jutta Elisabeth Boehmer, Bracknell (GB); Adrian Longstaff, Bracknell (GB); Timothy Robert Desson, Bracknell (GB); Sally Elizabeth Russell, Bracknell (GB); Matthew Brian Hotson, Bracknell (GB); Donn Warwick Moseley, Bracknell (GB); Claire Janet Russell, Bracknell (GB); Jake Goodwin-Tindall, Bracknell (GB)

(73) Assignees: Syngenta Limited, Guildford, Surrey (GB); Syngenta Participations AG, Basel (CH)

( * ) Notice: Subject to any disclaimer, the term of this patent is extended or adjusted under 35 U.S.C. 154(b) by 0 days.

(21) Appl. No.: 14/913,207

(22) PCT Filed: Aug. 14, 2014

(86) PCT No.: PCT/EP2014/067407
§ 371 (c)(1),
(2) Date: Feb. 19, 2016

(87) PCT Pub. No.: WO2015/024853
PCT Pub. Date: Feb. 26, 2015

(65) Prior Publication Data
US 2016/0200708 A1    Jul. 14, 2016

(30) Foreign Application Priority Data

Aug. 20, 2013    (IN) .......................... 2503/DEL/2013

(51) Int. Cl.
*C07D 403/04*    (2006.01)
*A01N 43/54*    (2006.01)

(52) U.S. Cl.
CPC ............ *C07D 403/04* (2013.01); *A01N 43/54* (2013.01)

(58) Field of Classification Search
CPC ............................ C07D 403/04; A01N 43/54
USPC ......................................................... 504/103
See application file for complete search history.

(56) References Cited

U.S. PATENT DOCUMENTS

| 4,302,239 A | 11/1981 | Lavanish |
| 4,600,430 A | 7/1986 | Abdulla et al. |
| 4,604,127 A | 8/1986 | Abdulla et al. |

*Primary Examiner* — Johann R Richter
*Assistant Examiner* — Courtney Brown
(74) *Attorney, Agent, or Firm* — James Cueva

(57) ABSTRACT

The invention relates to pyrrolone compounds of the formula (I) wherein X, $R^1$, $R^2$, $R^3$, $R^a$, $R^c$ and $R^d$ are as defined in the specification. Furthermore, the present invention relates to processes and intermediates for making compounds of formula (I), to herbicidal compositions comprising these compounds and to methods of using these compounds to control plant growth.

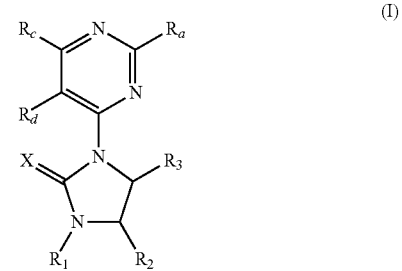

14 Claims, No Drawings

CHEMICAL COMPOUNDS

RELATED APPLICATION INFORMATION

This application is a 371 national stage entry of International Application No. PCT/EP2014/067407 filed Aug. 14, 2014, which claims priority to 2503/DEL/2013, filed Aug. 20, 2013, the contents of which are incorporated herein by reference herein.

The present invention relates to certain substituted dihydro-hydantoin derivatives, to processes for their preparation, herbicidal compositions comprising them, and their use in controlling plants or inhibiting plant growth.

Herbicidal dihydro-hydantoins of the formula

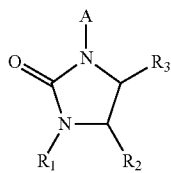

wherein A is a pyridine ring are taught in U.S. Pat. No. 4,600,430. Similar compounds wherein A is a pyridazine ring are taught in U.S. Pat. No. 4,604,127.

SUMMARY OF THE INVENTION

In a first aspect, the invention provides compounds of the formula (I)

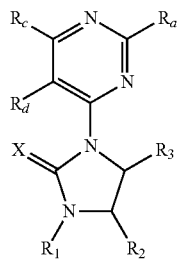

wherein
X is selected from S and O;
$R^a$ is selected from hydrogen and halogen;
$R^c$ is selected from hydrogen, formyl, hydroxyl, halogen, nitro, cyano, $C_1$-$C_8$ alkyl, $C_1$-$C_6$ cyanoalkyl, $C_1$-$C_6$ haloalkyl, $C_1$-$C_6$ hydroxyalkyl, $C_2$-$C_6$ alkenyloxy $C_1$-$C_6$ alkyl, $C_1$-$C_6$ alkylthio, $C_1$-$C_6$ alkoxy, $C_1$-$C_6$ alkoxy $C_1$-$C_6$ alkyl, $C_1$-$C_6$ alkthio $C_1$-$C_6$ alkyl, $C_1$-$C_6$ cyanoalkoxy, $C_1$-$C_6$ haloalkoxy, $C_1$-$C_6$ alkoxy $C_1$-$C_6$ alkoxy, $C_2$-$C_8$ alkenyl, $C_2$-$C_8$ alkynyl, $C_2$-$C_6$ cyanoalkenyl, $C_2$-$C_6$ cyanoalkynyl, $C_2$-$C_6$ alkenyloxy, $C_2$-$C_6$ alkynyloxy, $C_2$-$C_6$ haloalkenyl, $C_2$-$C_6$ haloalkynyl, $C_2$-$C_6$ haloalkenyloxy, $C_2$-$C_6$ haloalkynyloxy, $C_1$-$C_6$ alkoxy $C_2$-$C_6$ alkenyl, $C_1$-$C_6$ alkoxy $C_2$-$C_6$ alkynyl, $C_r$ $C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylsulfonyloxy, $C_1$-$C_6$ alkylcarbonyl, $C_1$-$C_6$ haloalkylcarbonyl, $C_2$-$C_6$ alkenylcarbonyl, $C_2$-$C_6$ alkynylcarbonyl, $C_2$-$C_6$ haloalkenylcarbonyl, $C_2$-$C_6$ haloalkynylcarbonyl, tri $C_1$-$C_6$ alkylsilyl $C_2$-$C_6$ alkynyl, a group $R^5R^6N$—, a group $R^5C(O)N(R^6)$—, a group $R^5S(O_2)N(R^6)$—, a group $R^5R^6NSO_2$—, a group $R^5R^6NC(O)$ $C_1$-$C_6$ alkyl, a $C_6$-$C_{10}$ aryloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ aryl $C_1$-$C_3$ alkyl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ benzyloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_3$-$C_6$ heterocyclyl group optionally substituted by from 1 to 3 groups independently selected from $C_1$-$C_4$ alkyl, a $C_3$-$C_6$ cycloalkyl group optionally substituted with from 1 to 3 groups independently selected from halogen, cyano, $C_1$-$C_6$ alkoxy and $C_1$-$C_6$ alkyl and a $C_3$-$C_6$ cycloalkenyl group optionally substituted with from 1 to 3 groups independently selected from halogen, cyano, $C_1$-$C_6$ alkoxy and $C_1$-$C_6$ alkyl;

$R^d$ is selected from hydrogen, halogen, cyano, $C_1$-$C_6$ alkyl and $C_1$-$C_6$ haloalkyl;

or $R^c$ and $R^d$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl;

$R^1$ is selected from hydrogen, $C_1$-$C_6$ alkyl optionally substituted with $NR^{10}R^{11}$, $C_1$-$C_3$ haloalkyl and $C_1$-$C_6$ alkoxy; wherein $R^{10}$ and $R^{11}$ are independently selected from hydrogen, $C_1$-$C_6$ alkyl and $C_1$-$C_6$ haloalkyl.

$R^2$ is selected from hydrogen, hydroxyl, halogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ alkoxy $C_1$-$C_6$ alkyl, $C_1$-$C_6$ cyanoalkyl and the group —$NR^{12}R^{13}$, wherein $R^{12}$ and $R^{13}$ are independently selected from hydrogen and $C_1$-$C_6$ alkyl.

or $R^1$ and $R^2$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from hydroxyl, =O, $C_1$-$C_6$ alkyl or $C_1$-$C_6$ haloalkyl.

$R^3$ is selected from halogen, hydroxyl, —$NR^{14}R^{15}$, $C_1$-$C_6$ alkoxy or any one of the following groups

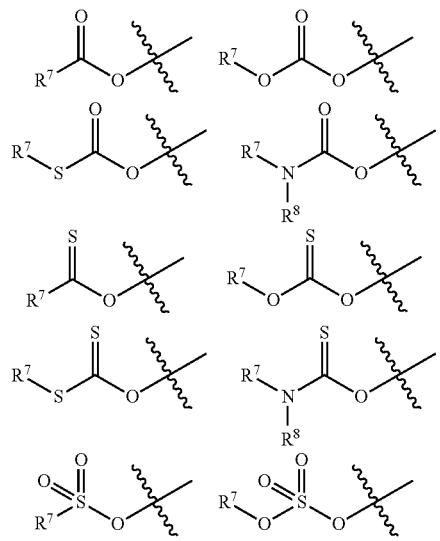

-continued

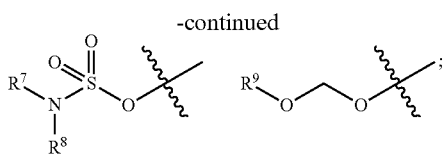

R$^5$ and R$^6$ are independently selected from hydrogen, C$_1$-C$_6$ alkyl, C$_1$-C$_6$ haloalkyl, C$_2$-C$_6$ alkenyl, C$_2$-C$_6$ alkynyl, or R$^5$ and R$^6$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen and C$_1$-C$_6$ alkyl;

R$^7$ and R$^8$ are independently selected from hydrogen, C$_1$-C$_6$ alkyl, C$_1$-C$_6$ haloalkyl, C$_2$-C$_6$ alkenyl, C$_2$-C$_6$ alkynyl, a C$_5$-C$_{10}$ heteroaryl group which can be mono- or bicyclic comprising from 1 to 4 heteroatoms independently selected from N, O and S and optionally substituted with 1 to 3 groups independently selected from halogen, C$_1$-C$_3$ alkyl, C$_1$-C$_3$ haloalkyl and C$_1$-C$_3$ alkoxy, a C$_6$-C$_{10}$ aryl group optionally substituted with 1 to 3 groups independently selected from halogen, nitro, cyano, C$_1$-C$_3$ alkyl, C$_1$-C$_3$ alkoxy, C$_1$-C$_3$ haloalkyl and C$_1$-C$_3$ haloalkoxy, or R$^7$ and R$^8$ together with the atoms to which they are attached form a 3-6 membered saturated or partially unsaturated ring optionally comprising from 1 to 3 heteroatoms independently selected from S, O and N and optionally substituted with from 1 to 3 groups independently selected from halogen or C$_1$-C$_6$ alkyl;

R$^9$ is selected from C$_1$-C$_6$ alkyl or benzyl optionally substituted with 1 to 3 groups independently selected from halogen, nitro, cyano, C$_1$-C$_3$ alkyl, C$_1$-C$_3$ alkoxy, C$_1$-C$_3$ haloalkyl and C$_1$-C$_3$ haloalkoxy;

R$^{14}$ and R$^{15}$ are, independently, selected from hydrogen, C$_1$-C$_{20}$ alkyl, C$_1$-C$_{20}$ haloalkyl, C$_2$-C$_{20}$ alkenyl, C$_2$-C$_{20}$ alkynyl, or R$^{14}$ and R$^{15}$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen and C$_1$-C$_6$ alkyl; or an N-oxide or salt form thereof.

In a second aspect, the invention provides herbicidal compositions comprising a compound of the invention together with at least one agriculturally acceptable adjuvant or diluent.

In a third aspect, the invention provides the use of a compound or a composition of the invention for use as a herbicide.

In a fourth aspect, the invention provides a method of controlling weeds in crops of useful plants, comprising applying to said weeds or to the locus of said weeds, or to said useful crop plants, a compound or a composition of the invention.

In a fifth aspect, the invention relates to processes useful in the preparation of compounds of the invention.

In a sixth aspect, the invention relates to intermediates useful in the preparation of compounds of the invention.

DETAILED DESCRIPTION

In particularly preferred embodiments of the invention, the preferred groups for X, R$^a$, R$^c$, R$^d$, R$^1$, R$^2$ and R$^3$, in any combination thereof, are as set out below.

Preferably, X is O.

Preferably R$^a$ is hydrogen.

Preferably, R$^c$ is selected from C$_1$-C$_8$ alkyl, C$_1$-C$_6$ haloalkyl, C$_2$-C$_8$ alkenyl, C$_1$-C$_6$ cyanoalkyl, C$_1$-C$_6$ alkoxy, C$_1$-C$_6$ hydroxyalkyl, C$_1$-C$_6$ alkoxy C$_1$-C$_6$ alkyl, C$_2$-C$_6$ alkenyloxy C$_1$-C$_6$ alkyl, C$_3$-C$_6$ cycloalkyl optionally substituted by from 1 to 3 groups independently selected from cyano, C$_1$-C$_3$ alkyl and C$_1$-C$_3$ alkoxy and a group R$^5$R$^6$NC (O) C$_1$-C$_6$ alkyl.

More preferably, R$^c$ is selected from C$_1$-C$_8$ alkyl, C$_1$-C$_6$ haloalkyl, C$_2$-C$_8$ alkenyl, C$_1$-C$_6$ cyanoalkyl, C$_1$-C$_6$ alkoxy C$_1$-C$_6$ alkyl and C$_3$-C$_6$ cycloalkyl optionally substituted by from 1 to 3 groups independently selected from cyano and C$_1$-C$_3$ alkyl.

More preferably, R$^c$ is selected from C$_1$-C$_8$ alkyl, C$_1$-C$_6$ haloalkyl, C$_2$-C$_8$ alkenyl, C$_1$-C$_6$ cyanoalkyl and C$_3$-C$_6$ cycloalkyl optionally substituted by from 1 to 3 groups independently selected from cyano and C$_1$-C$_3$ alkyl.

Even more preferably, R$^c$ is selected from C$_1$-C$_6$ alkyl, C$_1$-C$_3$ haloalkyl, C$_1$-C$_6$ cyanoalkyl and C$_3$-C$_6$ cycloalkyl optionally substituted by from 1 to 3 groups independently selected from cyano and C$_1$-C$_3$ alkyl.

Even more preferably R$^c$ is selected from methyl, ethyl, iso-propyl, (2-methyl)-prop-1-yl, (1-methyl)-prop-1-yl, tert-butyl, (1,1-dimethyl)-prop-1-yl, (1,1-dimethyl)-but-1-yl, (1-methyl-1-ethyl)-prop-1-yl, cyclobutyl, cyclopropyl, (1-methyl)cycloprop-1-yl, (1-methyl-1-cyano)-eth-1-yl, (1-methyl-1-ethyl-2-cyano)-prop-1-yl, (1,1-dimethyl-2-cyano)-prop-1-yl, 1-fluoroethyl, 1,1-difluoroethyl, difluoromethyl, 1-fluoro-1-methylethyl and trifluoromethyl.

Even more preferably R$^c$ is selected from methyl, ethyl, iso-propyl, (2-methyl)-prop-1-yl, (1-methyl)-prop-1-yl, tert-butyl, (1,1-dimethyl)-prop-1-yl, (1,1-dimethyl)-but-1-yl, (1-methyl-1-ethyl)-prop-1-yl, cyclobutyl, cyclopropyl, (1-methyl)cycloprop-1-yl, (1-methyl-1-cyano)-eth-1-yl, (1-methyl-1-ethyl-2-cyano)-prop-1-yl, (1,1-dimethyl-2-cyano)-prop-1-yl, 1-fluoroethyl, 1,1-difluoroethyl, difluoromethyl, 1-fluoro-1-methylethyl, trifluoromethyl and 1-chloro-1-methylethyl.

Most preferably, R$^c$ is selected from tert-butyl, (1-methyl-1-cyano)-eth-1-yl, 1,1-difluoroethyl, 1-fluoro-1-methylethyl and trifluoromethyl.

Preferably, R$^d$ is hydrogen.

In particular, the substituted pyrimidine may be 6-tert-butylpyrimidin-4-yl, 6-(1-fluoro-1-methyl-ethyl)pyrimidin-4-yl, 6-((1-methyl-1-cyano)eth-1yl)pyrimidin-4-yl or 6-(1, 1-difluoroethyl)pyrimidin-4-yl.

Preferably R$^1$ is C$_1$-C$_3$ alkyl, C$_1$-C$_3$ alkoxy or C$_1$-C$_3$ haloalkyl. More preferably R$^1$ is methyl or methoxy.

Preferably R$^2$ is hydrogen, hydroxyl, C$_1$-C$_3$ alkyl, C$_1$-C$_3$ alkoxy, C$_1$-C$_3$ haloalkyl, C$_1$-C$_3$ haloalkoxy allyl. More preferably R$^2$ is hydrogen, methyl or ethoxy.

In one embodiment, preferably, R$^3$ is selected from halogen, hydroxyl, or any one of the following groups

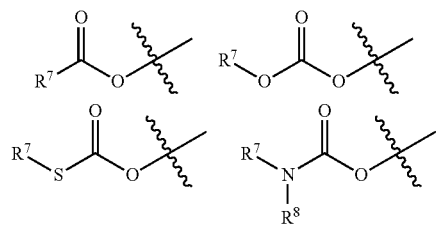

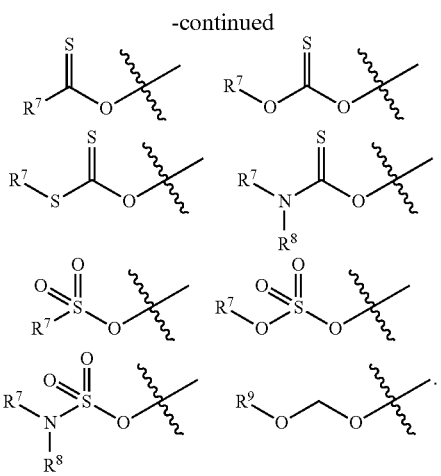

In this embodiment, preferably, $R^3$ is selected from halogen, hydroxyl, or any of the following groups

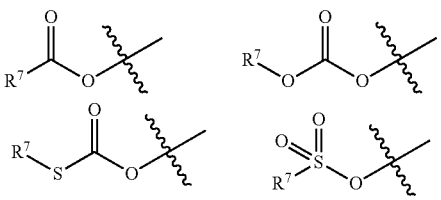

$R^7$ may be as defined above but preferably, $R^7$ is selected from $C_1$-$C_6$ alkyl, $C_1$-$C_6$ haloalkyl, $C_2$-$C_6$ alkenyl, $C_2$-$C_6$ alkynyl, a $C_5$-$C_{10}$ monocyclic heteroaryl group comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy, a $C_6$-$C_{10}$ aryl group optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy.

More preferably, $R^3$ is selected from hydroxyl, halogen, $C_1$-$C_6$ alkylcarbonyloxy, $C_1$-$C_6$ alkoxycarbonyloxy or aryloxycarbonyloxy wherein the aryl group may be substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy.

Even more preferably, $R^3$ is selected from hydroxyl or halogen.

Most preferably, $R^3$ is hydroxyl.

In another embodiment, preferably, $R^3$ is selected from halogen, hydroxyl, —NR$^{14}$R$^{15}$, $C_1$-$C_6$ alkoxy or any of the following groups

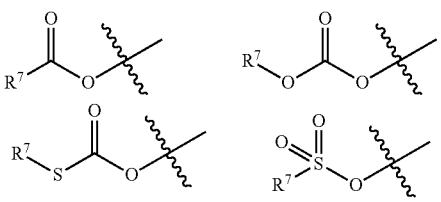

$R^7$ may be as defined above but preferably, $R^7$ is selected from $C_1$-$C_6$ alkyl, $C_1$-$C_6$ haloalkyl, $C_2$-$C_6$ alkenyl, $C_2$-$C_6$ alkynyl, a $C_5$-$C_{10}$ monocyclic heteroaryl group comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy, a $C_6$-$C_{10}$ aryl group optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy.

More preferably, $R^3$ is selected from hydroxyl, halogen, —NR$^{14}$R$^{15}$, $C_1$-$C_6$ alkylcarbonyloxy, $C_1$-$C_6$ alkoxycarbonyloxy or aryloxycarbonyloxy wherein the aryl group may be substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy.

Even more preferably, $R^3$ is selected from hydroxyl or halogen. Most preferably, $R^3$ is hydroxyl.

The compounds of formula (I) may exist as different geometric isomers, or in different tautomeric forms. This invention covers all such isomers and tautomers, and mixtures thereof in all proportions, as well as isotopic forms such as deuterated compounds.

The compounds of this invention may contain one or more asymmetric centers and may thus give rise to optical isomers and diastereomers. While shown without respect to stereochemistry, the present invention includes all such optical isomers and diastereomers as well as the racemic and resolved, enantiomerically pure R and S stereoisomers and other mixtures of the R and S stereoisomers and agrochemically acceptable salts thereof. It is recognized certain optical isomers or diastereomers may have favorable properties over the other. Thus when disclosing and claiming the invention, when a racemic mixture is disclosed, it is clearly contemplated that both optical isomers, including diastereomers, substantially free of the other, are disclosed and claimed as well.

Alkyl, as used herein refers to an aliphatic hydrocarbon chain and includes straight and branched chains e. g. of 1 to 8 carbon atoms such as methyl, ethyl, n-propyl, isopropyl, n-butyl, isobutyl, sec-butyl, t-butyl, n-pentyl, isopentyl, neopentyl, n-hexyl, and isohexyl.

Alkenyl, as used herein, refers to an aliphatic hydrocarbon chain having at least one double bond, and preferably one double bond, and includes straight and branched chains e. g. of 2 to 8 carbon atoms such as ethenyl (vinyl), prop-1-enyl, prop-2-enyl (allyl), isopropenyl, but-1-enyl, but-2-enyl, but-3-enyl, 2-methypropenyl.

Alkynyl, as used herein, refers to an aliphatic hydrocarbon chain having at least one triple bond, and preferably one triple bond, and includes straight and branched chains e. g. of 2 to 8 carbon atoms such as ethynyl, prop-1-ynyl, prop-2-ynyl (propargyl) but-1-ynyl, but-2-ynyl and but-3-ynyl.

Cycloalkyl, as used herein, refers to a cyclic, saturated hydrocarbon group having from 3 to 6 ring carbon atoms. Examples of cycloalkyl groups are cyclopropyl, cyclobutyl, cyclopentyl and cyclohexyl.

Cycloalkenyl, as used herein, refers to a cyclic, partially unsaturated hydrocarbon group having from 3 to 6 ring carbon atoms.

Alkoxy as used herein refers to the group —OR, wherein R is alkyl as defined above. Examples of alkoxy groups include methoxy, ethoxy, n-propoxy, isopropoxy, n-butoxy, isobutoxy, sec-butoxy, t-butoxy, n-pentoxy, isopentoxy, neopentoxy, n-hexyloxy, and isohexyloxy.

Alkenyloxy refers to the group —OR, wherein R is alkenyl as defined above. Examples of alkenyloxy groups are ethenyloxy, propenyloxy, isopropenyloxy, but-1-enyloxy, but-2-enyloxy, but-3-enyloxy, 2-methypropenyloxy etc.

Alkynyloxy refers to the group —OR, wherein R is alkynyl is as defined above. Examples of alkynyloxy groups are ethynyloxy, propynyloxy, but-1-ynyloxy, but-2-ynyloxy and but-3-ynyloxy.

Alkoxyalkyl as used herein refers to the group —ROR, wherein each R is, independently, an alkyl group as defined above.

Alkoxyalkenyl as used herein refers to the group —ROR', wherein R is an alkyl group as defined above and R' is an alkenyl group as defined above.

Alkoxyalkynyl as used herein refers to the group —ROR', wherein R is an alkyl group as defined above and R' is an alkynyl group as defined above.

Alkoxyalkoxy, as used herein, refers to the group —OROR, wherein each R is, independently, an alkyl group as defined above.

Cyanoalkyl as used herein refers to an alkyl group substituted with one or more cyano groups.

Cyanoalkenyl as used herein refers to an alkenyl group substituted with one or more cyano groups.

Cyanoalkynyl as used herein refers to an alkynyl group substituted with one or more cyano groups.

Cyanocycloalkyl as used herein refers to an cycloalkyl group substituted with one or more cyano groups.

Cyanoalkoxy as used herein refers to the group —OR, wherein R is cyanoalkyl as defined above.

Halogen, halide and halo refer to iodine, bromine, chlorine and fluorine.

Haloalkyl as used herein refers to an alkyl group as defined above wherein at least one hydrogen atom has been replaced with a halogen atom as defined above. Examples of haloalkyl groups include chloromethyl, dichloromethyl, trichloromethyl, fluoromethyl, difluoromethyl and trifluoromethyl. Preferred haloalkyl groups are fluoroalkyl groups {i.e. haloalkyl groups, containing fluorine as the only halogen). More highly preferred haloalkyl groups are perfluoroalkyl groups, i.e. alkyl groups wherein all the hydrogen atoms are replaced with fluorine atoms.

Haloalkenyl as used herein refers to an alkenyl group as defined above wherein at least one hydrogen atom has been replaced with a halogen atom as defined above.

Haloalkynyl as used herein refers to an alkynyl group as defined above wherein at least one hydrogen atom has been replaced with a halogen atom as defined above.

Haloalkoxy as used herein refers to the group —OR, wherein R is haloalkyl as defined above.

Haloalkenyloxy as used herein refers to the group —OR, wherein R is haloalkenyl as defined above.

Haloalkynyloxy as used herein refers to the group —OR, wherein R is haloalkynyl as defined above.

Alkylthio as used herein refers to the group —SR, wherein R is an alkyl group as defined above. Alkylthio groups include, but are not limited to, methylthio, ethylthio, propylthio, tertbutylthio, and the like.

Alkylthioalkyl as used herein refers to the group —RSR, wherein each R is, independently, an alkyl group as defined above.

Haloalkylthio as used herein refers to the group —SR, wherein R is a haloalkyl group as defined above.

Alkylsulfinyl as used herein refers to the group —S(O)R, wherein R is an alkyl group as defined above.

Alkylsulfonyl as used herein refers to the group —S(O)$_2$R, wherein R is an alkyl group as defined above.

Haloalkylsulfinyl as used herein refers to the group —S(O)R, wherein R is a haloalkyl group as defined above.

Haloalkylsulfonyl as used herein refers to the group —S(O)$_2$R, wherein R is a haloalkyl group as defined above.

Alkylsulfonyloxy, as used herein refers to the group —OSO$_2$R, wherein R is an alkyl group as defined above.

Alkylcarbonyl, as used herein refers to the group —COR, wherein R is an alkyl group as defined above. Examples of alkylcarbonyl groups include ethanoyl, propanoyl, n-butanoyl, etc.

Alkenylcarbonyl, as used herein refers to the group —COR, wherein R is an alkenyl group as defined above.

Alkynylcarbonyl, as used herein refers to the group —COR, wherein R is an alkynyl group as defined above.

Haloalkylcarbonyl, as used herein refers to the group —COR, wherein R is a haloalkyl group as defined above.

Haloalkenylcarbonyl, as used herein refers to the group —COR, wherein R is a haloalkenyl group as defined above.

Haloalkynylcarbonyl, as used herein refers to the group —COR, wherein R is a haloalkynyl group as defined above.

Alkoxycarbonyloxy as used herein, refers to the group —OC(O)OR, wherein R is an alkyl group as defined above. Examples of alkoxycarbonyloxy groups are methoxycarbonyloxy, ethoxycarbonyloxy, propoxycarbonyloxy, but-1-oxycarbonyloxy, but-2-oxycarbonyloxy and but-3-oxycarbonyloxy.

Trialkylsilylalkynyl, as used herein, refers to the group —RSi(R')$_3$, wherein R is an alkynyl group as defined above and each R' is, independently, selected from an alkyl group as defined above.

Formyl, as used herein, refers to the group —C(O)H.

Hydroxy or hydroxyl, as used herein, refers to the group —OH.

Nitro, as used herein, refers to the group —NO$_2$.

Cyano as used herein, refers to the group —CN.

Aryl, as used herein, refers to an unsaturated aromatic carbocyclic group of from 6 to 10 carbon atoms having a single ring (e. g., phenyl) or multiple condensed (fused) rings, at least one of which is aromatic (e.g., indanyl, naphthyl). Preferred aryl groups include phenyl, naphthyl and the like. Most preferably, an aryl group is a phenyl group.

Aryloxy, as used herein, refers to the group —O-aryl, wherein aryl is as defined above. Preferred aryloxy groups include phenoxy, naphthyloxy and the like.

Aryloxycarbonyloxy as used herein, refers to the group —OC(O)O-aryl wherein aryl is a as defined above.

Benzyl, as used herein, refers to the group —CH$_2$C$_6$H$_5$.

Benzyloxy, as used herein, refers to the group —OCH$_2$C$_6$H$_5$.

Heterocyclyl, as used herein, refers to a non-aromatic ring system containing 3 to 10 ring atoms, at least one ring heteroatom and consisting either of a single ring or of two or more fused rings. Preferably, single rings will contain up to three and bicyclic systems up to four heteroatoms which will preferably be chosen from nitrogen, oxygen and sulfur. Examples of such groups include pyrrolidinyl, imidazolinyl, pyrazolidinyl, piperidyl, piperazinyl, quinuclidinyl, morpholinyl, together with unsaturated or partially unsaturated analogues such as 4,5,6,7-tetrahydro-benzothiophenyl, chromen-4-onyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl.

Heteroaryl, as used herein, refers to a ring system containing 5 to 10 ring atoms, 1 to 4 ring heteroatoms and consisting either of a single aromatic ring or of two or more fused rings, at least one of which is aromatic. Preferably, single rings will contain up to three and bicyclic systems up to four heteroatoms which will preferably be independently chosen from nitrogen, oxygen and sulfur. Examples of such groups include pyridyl, pyridazinyl, pyrimidinyl, pyrazinyl, triazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. Examples of bicyclic groups are benzothiophenyl, benzimidazolyl, benzothiadiazolyl, quinolinyl, cinnolinyl, quinoxalinyl and pyrazolo[1,5-a]pyrimidinyl.

'Saturated ring', as used herein, refers to a ring system in which the atoms in the ring are linked by single bonds.

'Partially unsaturated ring', as used herein, refers to a ring system in which at least two atoms in the ring are linked by a double bond. Partially unsaturated ring systems do not include aromatic rings.

"Optionally substituted" as used herein means the group referred to can be substituted at one or more positions by any one or any combination of the radicals listed thereafter. For most groups, one or more hydrogen atoms are replaced by the radicals listed thereafter. For halogenated groups, for example, haloalkyl groups, one or more halogen atoms are replaced by the radicals listed thereafter.

Suitable salts include those derived from alkali or alkaline earth metals and those derived from ammonia and amines. Preferred cations include sodium, potassium, magnesium, and ammonium cations of the formula $N^+(R^{19}R^{20}R^{21}R^{22})$ wherein $R^{19}$, $R^{20}$, $R^{21}$ and $R^{22}$ are independently selected from hydrogen, $C_1$-$C_6$ alkyl and $C_1$-$C_6$ hydroxyalkyl. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of Formula I because they are water-soluble and lend themselves to the preparation of desirable aqueous based herbicidal compositions.

Acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety.

In another aspect the present invention provides intermediates useful in the preparation of compounds of the invention.

In one embodiment, there are provided intermediates of the formula (III), wherein $R^1$, $R^2$, $R^a$, $R^c$ and $R^d$ are as defined above. These intermediates can also display herbicidal activity.

Compounds of the invention may be prepared by techniques known to the person skilled in the art of organic chemistry. General methods for the production of compounds of formula (I) are described below. Unless otherwise stated in the text, the substituents X, $R^1$, $R^2$, $R^3$, $R^a$, $R^c$ and $R^d$ are as defined hereinbefore. The starting materials used for the preparation of the compounds of the invention may be purchased from usual commercial suppliers or may be prepared by known methods. The starting materials as well as the intermediates may be purified before use in the next step by state of the art methodologies such as chromatography, crystallization, distillation and filtration.

For example, compounds of formula (IX) wherein $R^1$ is an alkyl or alkoxy group and $R^2$ is a hydrogen or alkyl group may be prepared by reaction of amino-pyrimidine (IV) with phenylchloroformate to give carbamate product (V). The subsequent reaction with an appropriately substituted amino-ester (VI) gives compounds of type (VII) and subsequent cyclisation gives compounds of type (VIII) and reduction with e.g. with sodium borohydride gives compounds of type (IX). The methyl amino-ester (VI) may also be replaced by other amino esters or amino-acids. Phenyl chloroformate may be replaced by other activating groups such as phosgene or para-nitrophenyl chlorofomate. The cyclisation to (VIII) may occur in situ or require heating for carboxylic acids or esters or treatment with a reagent such as thionyl chloride for carboxylic acids. Compounds of type (VII) can be converted to compounds of type (IX) directly by treatment with a reducing reagent such as DIBAL-H or NaBH$_4$.

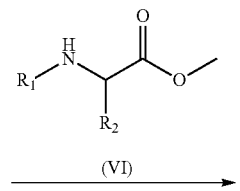

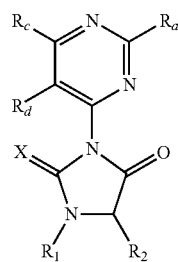

(III)

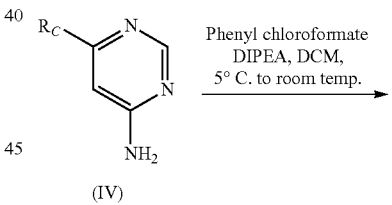

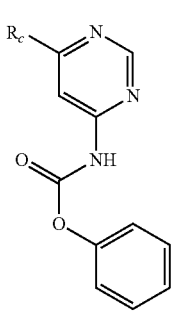

(V)

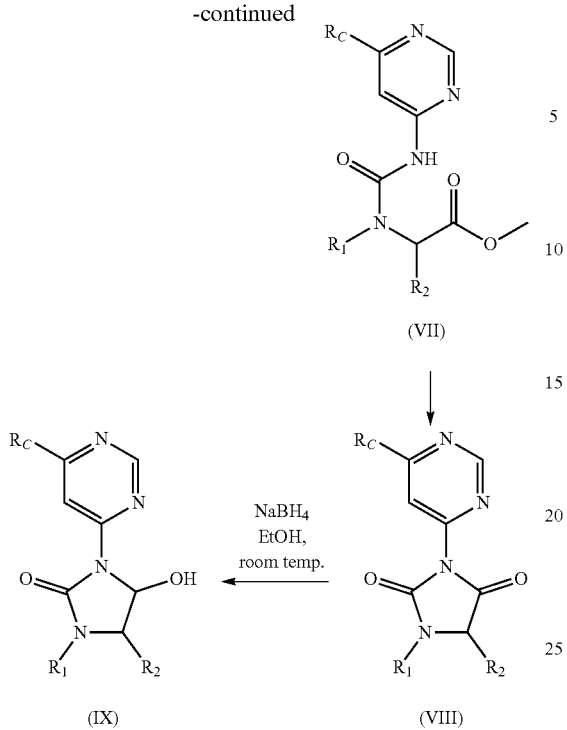
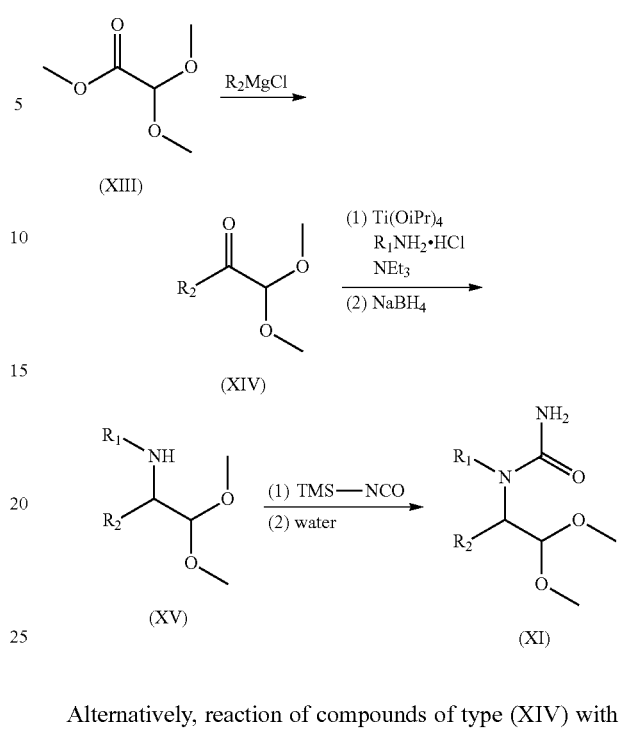

Alternatively, compounds of formula (IX) wherein $R^1$ is an alkyl group or alkoxy group and $R^2$ is a hydrogen or alkyl group may be prepared by Palladium catalysed reaction of chloro-pyrimidine (X) with urea (XI) to give (XII) (for a reference to a related reaction see WO2006048249, example 3.1) and then subsequent cyclisation gives compounds of type (IX).

Alternatively, reaction of compounds of type (XIV) with methoxylamine following by reduction of the oxime ether formed gives compounds of type (XV) which can form compounds of type (XI) where R1 is alkoxy. Alternatively, reaction of compounds of type (XIV) where R2 is hydrogen with methoxylamine followed by addition of Grignard reagents to the formed oxime also can give compounds of type (XV).

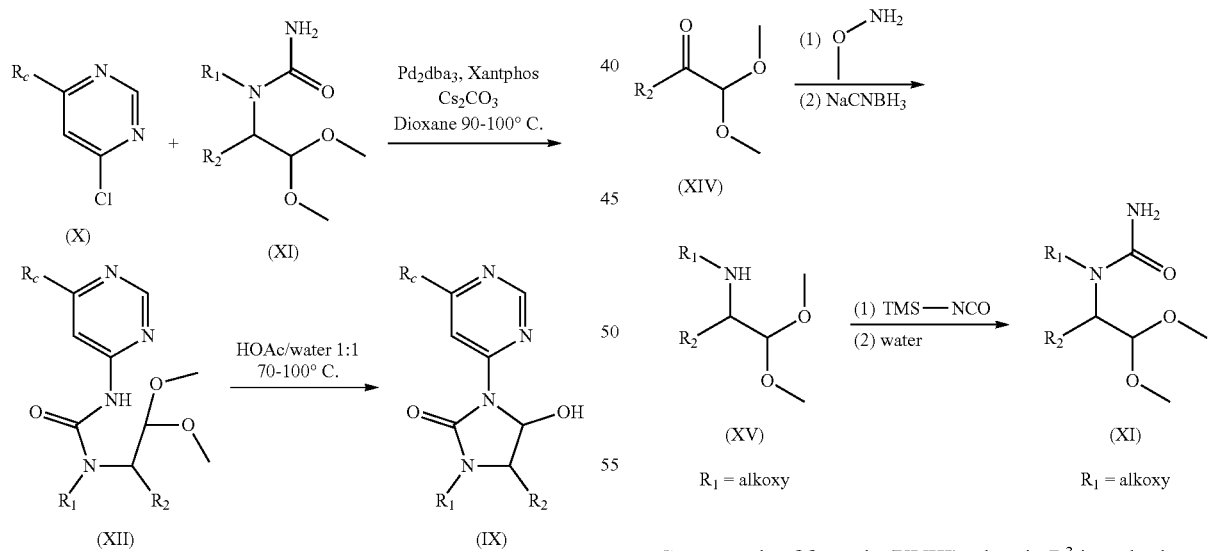

Urea (XI) may be formed by reaction of ester (XIII) with Grignard reagents, reductive amination of the product ketone (XIV) with amines and finally reaction of the subsequent product amine (XV) with TMS-isocyanate to give compounds of type (XI). Alternatively (XV) can be formed by a Grignard addition of type $R_2MgCl$ to appropriate imines. Alternatively, a nitrile can replace the ester group of (XIII) in the reaction with Grignard reagents.

Compounds of formula (XVIII) wherein $R^3$ is an hydroxy group may be prepared by the Palladium catalysed reaction of chloro-pyrimidine (X) with urea (XVI) to give urea (XVII) (for a reference to a related reaction see WO2006048249, example 3.1), which can react with aqueous glyoxal solution to give product (XVIII). Compounds of formula (IX) where $R_2$ is an alkoxy group may be prepared by reacting compounds of formula (XVIII) with alcohols of type $R_4$—OH under acidic conditions.

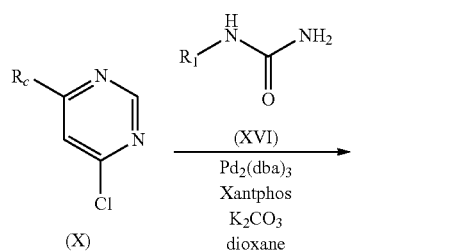

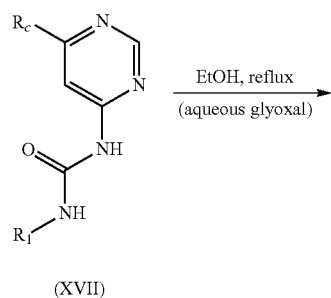

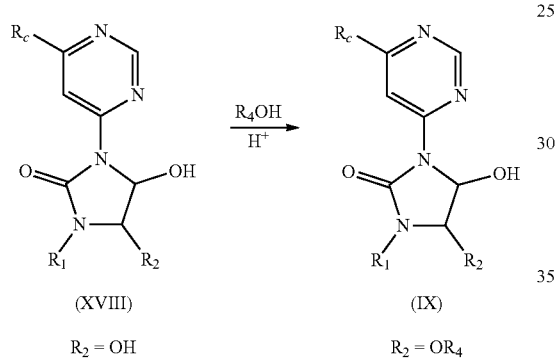

Alternatively, compounds of formula (V) may be reacted with compounds of formula (XIX) wherein R² is a hydrogen or alkyl group to give products of type (XX). Cyclisation with a suitable reagent such as thionyl chloride gives compounds of formula (XXI), which can be alkylated with a suitable base such as LiHMDS and a suitable alkylating agent such as methyl iodide (for R₁=Me) to give compound (VIII). Reduction as before gives compounds of type (IX).

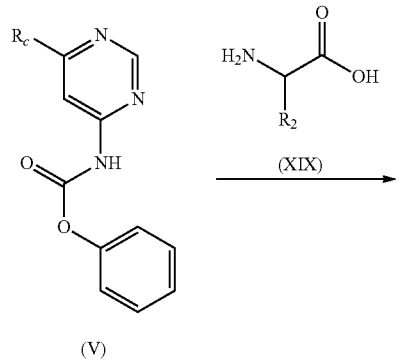

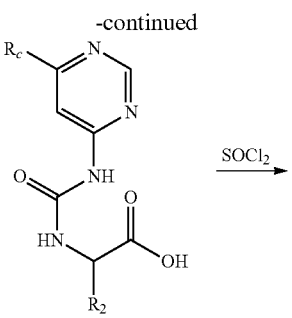

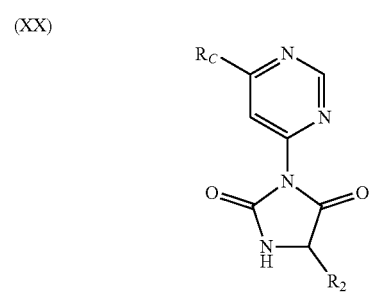

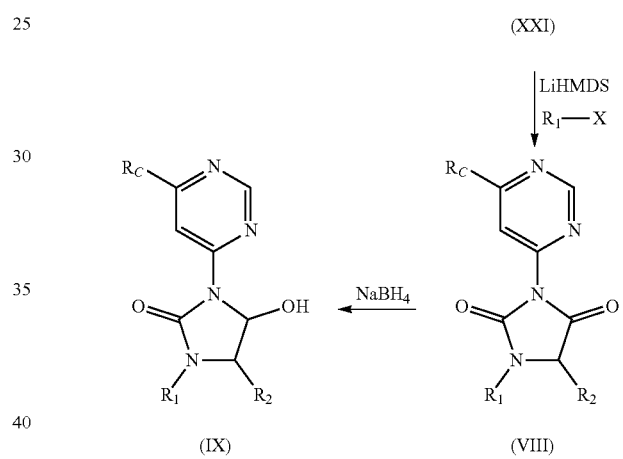

Alternatively oxidative cleavage (using ozonolysis or OsO₄/NaIO₄ or similar conditions) of an appropriate vinyl compound such as (XXII) or derivatives thereof and cyclisation could give the desired product.

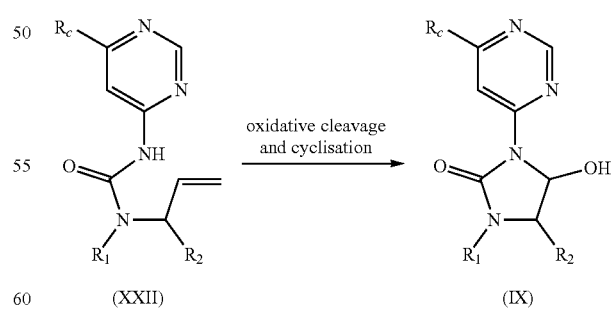

Alternatively, compounds of type (XXIII) may be coupled with compounds of type (X) under transition metal catalysis such as Palladium catalysed conditions to give compounds of type (VIII) and then standard reduction with NaBH₄ for example gives products of type (IX).

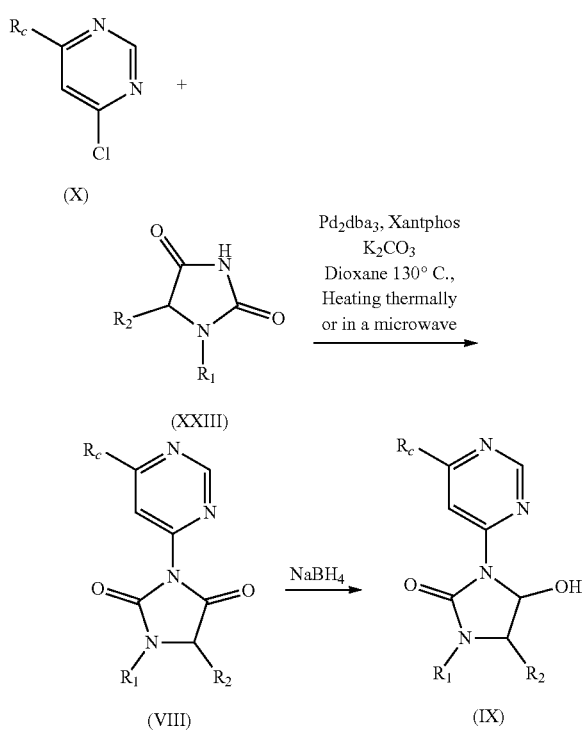

Amino and chloro-pyrimidines may be made by standard procedures such as those outlined below.

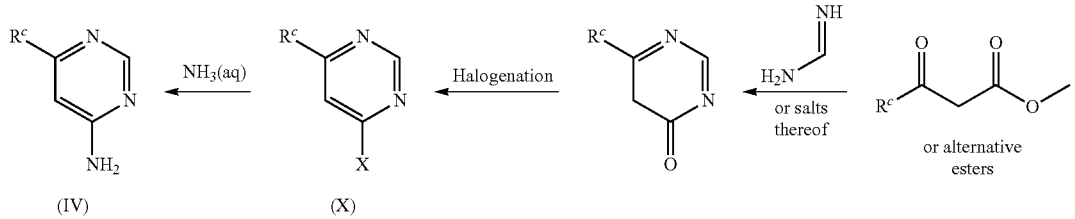

Suitable conditions for effecting these transformations are set out in texts such as J. March, Advanced Organic Chemistry, 4th ed. Wiley, New York, 1992.

The compounds of formula (I) according to the invention can be used as herbicides in unmodified form, as obtained in the synthesis, but they are generally formulated into herbicidal compositions in various ways using formulation adjuvants, such as carriers, solvents and surface-active substances. Therefore, the invention also relates to a herbicidal composition which comprises a herbicidally effective amount of a compound of formula (I) in addition to formulation adjuvants. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. Such formulations can either be used directly or they are diluted prior to use. The dilutions can be made, for example, with water, liquid fertilizers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art in this connection. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydro-furfuryl alcohol, hexanol, octanol, ethylene glycol, propylene glycol, glycerol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecyl-benzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further adjuvants that can usually be used in pesticidal formulations include crystallization inhibitors, viscosity modifiers, suspending agents, dyes, anti-oxidants, foaming agents, light absorbers, mixing auxiliaries, antifoams, complexing agents, neutralizing or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilizers.

The compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combination with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltriloxanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say, without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-trate®, to be added to the spray mixture as action-enhancing agent.

The herbicidal compositions generally comprise from 0.1 to 99% by weight, especially from 0.1 to 95% by weight, compounds of formula (I) and from 1 to 99.9% by weight of a formulation adjuvant which preferably includes from 0 to 25% by weight of a surface-active substance. Whereas commercial products will preferably be formulated as concentrates, the end user will normally employ dilute formulations.

The rates of application of compounds of formula (I) may vary within wide limits and depend on the nature of the soil, the method of application (pre- or post-emergence; seed dressing; application to the seed furrow; no tillage application etc.), the crop plant, the grass or weed to be controlled, the prevailing climatic conditions, and other factors governed by the method of application, the time of application and the target crop. The compounds of formula (I) according to the invention are generally applied at a rate of from 10 to 2000 g/ha, especially from 50 to 1000 g/ha.

Preferred formulations have especially the following compositions (%=percent by weight):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%
The following Examples further illustrate, but do not limit, the invention.
Formulation Examples for Herbicides of Formula (I) (%=% by Weight)

F1. Emulsifiable concentrates

| | a) | b) | c) | d) |
|---|---|---|---|---|
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

F2. Solutions

| | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for use in the form of microdrops.

F3. Wettable powders

| | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

F4. Coated granules

| | a) | b) | c) |
|---|---|---|---|
| active ingredient | 0.1% | 5% | 15% |
| highly dispersed silicic acid | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride and applied to the carrier by spraying, and the solvent is then evaporated off in vacuo.

F5. Coated granules

| | a) | b) | c) |
|---|---|---|---|
| active ingredient | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

F6. Extruder granules

| | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

F7. Dusts

| | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | | | | |
|---|---|---|---|---|
| | a) | b) | c) | d) |
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

The invention also provides a method of controlling plants which comprises applying to the plants or to the locus thereof a herbicidally effective amount of a compound of formula (I).

The invention also provides a method of inhibiting plant growth which comprises applying to the plants or to the locus thereof a herbicidally effective amount of a compound of formula (I).

The invention also provides a method of controlling weeds in crops of useful plants, comprising applying to said weeds or to the locus of said weeds, or to said useful plants or to the locus of said useful plants, a compound or a composition of the invention.

The invention also provides a method of selectively controlling grasses and/or weeds in crops of useful plants which comprises applying to the useful plants or locus thereof or to the area of cultivation a herbicidally effective amount of a compound of formula (I).

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example: killing, retardation, leaf burn, albinism, dwarfing and the like. The term "plants" refers to all physical parts of a plant, including seeds, seedlings, saplings, roots, tubers, stems, stalks, foliage, and fruits. The term "locus" is intended to include soil, seeds, and seedlings, as well as established vegetation and includes not only areas where weeds may already be growing, but also areas where weeds have yet to emerge, and also to areas under cultivation with respect to crops of useful plants. "Areas under cultivation" include land on which the crop plants are already growing and land intended for cultivation with such crop plants. The term "weeds" as used herein means any undesired plant, and thus includes not only agronomically important weeds as described below, but also volunteer crop plants.

The compounds of the invention can be applied before or after planting of the crops, before weeds emerge (pre-emergence application) or after weeds emerge (post-emergence application), and are particularly effective when applied post-emergence to the weeds.

Crops of useful plants in which the composition according to the invention can be used include, but are not limited to, perennial crops, such as citrus fruit, grapevines, nuts, oil palms, olives, pome fruit, stone fruit and rubber, and annual arable crops, such as cereals, for example barley and wheat, cotton, oilseed rape, maize, rice, soy beans, sugar beet, sugar cane, sunflowers, ornamentals, switchgrass, turf and vegetables, especially cereals, maize and soy beans.

The grasses and weeds to be controlled may be both monocotyledonous species, for example *Agrostis, Alopecurus, Avena, Brachiaria, Bromus, Cenchrus, Cyperus, Digitaria, Echinochloa, Eriochloa, Lolium, Monochoria, Panicum, Poa, Rottboellia, Sagittaria, Scirpus, Setaria, Sida* and *Sorghum*, and dicotyledonous species, for example *Abutilon, Amaranthus, Chenopodium, Chrysanthemum, Euphorbia, Galium, Ipomoea, Kochia, Nasturtium, Polygonum, Sida, Sinapis, Solanum, Stellaria, Veronica, Viola* and *Xanthium*.

In all aspects of the invention, in a particular embodiment, the weeds, e.g. to be controlled and/or growth-inhibited may be monocotyledonous or dicotyledonous weeds, which are tolerant or resistant to one or more other herbicides for example, HPPD inhibitor herbicides such as mesotrione, PSII inhibitor herbicides such as atrazine or EPSPS inhibitors such as glyphosate. Such weeds include, but are not limited to resistant *Amaranthus* biotypes.

Crops are to be understood as also including those crops which have been rendered tolerant to herbicides or classes of herbicides (e.g. auxins or ALS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®, respectively.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesize such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

Any method of application to weeds/crop of useful plant, or locus thereof, which is routinely used in agriculture may be used, for example application by spray or broadcast method typically after suitable dilution of a compound of formula (I) (whether said compound is formulated and/or in combination with one or more further active ingredients and/or safeners, as described herein).

The compounds of formula (I) according to the invention can also be used in combination with other active ingredients, e.g. other herbicides, and/or insecticides, and/or acaricides, and/or nematocides, and/or molluscicides, and/or fungicides, and/or plant growth regulators. Such mixtures, and the use of such mixtures to control weeds and/or undesired plant growth, form yet further aspects of the invention. For the avoidance of doubt, mixtures of invention also include mixtures of two or more different compounds of formula (I). In particular, the present invention also relates to a composition of the invention which comprises at least one further herbicide in addition to the compound of formula (I).

When a compound of formula (I) is combined with at least one additional herbicide, the following mixtures of the compound of formula (I) are preferred. Compound of formula (I)+acetochlor, compound of formula (I)+acifluorfen, compound of formula (I)+acifluorfen-sodium, compound of formula (I)+aclonifen, compound of formula (I)+acrolein, compound of formula (I)+alachlor, compound of formula (I)+alloxydim, compound of formula (I)+allyl alcohol, compound of formula (I)+ametryn, compound of formula (I)+amicarbazone, compound of formula (I)+amidosulfuron, compound of formula (I)+aminocyclopyrachlor, compound of formula (I)+aminopyralid, compound of formula (I)+amitrole, compound of formula (I)+ammonium sulfamate, compound of formula (I)+anilofos, compound of formula (I)+asulam, compound of formula (I)+atrazine, formula (I)+aviglycine, formula (I)+azafenidin, compound of formula (I)+azimsulfuron, compound of formula (I)+BCPC, compound of formula (I)+beflubutamid, compound of formula (I)+benazolin, formula (I)+bencarbazone, compound of formula (I)+benfluralin, compound of formula (I)+benfuresate, compound of formula (I)+bensulfuron, compound of formula (I)+bensulfuron-methyl, compound of formula (I)+bensulide, compound of formula (I)+bentazone, compound of formula (I)+benzfendizone, compound of formula (I)+benzobicyclon, compound of formula (I)+benzofenap, compound of formula (I)+bicyclopyrone, compound of formula (I)+bifenox, compound of formula (I)+bilanafos, compound of formula (I)+bispyribac, compound of formula (I)+bispyribac-sodium, compound of formula (I)+borax, compound of formula (I)+bromacil, compound of formula (I)+bromobutide, formula (I)+bromophenoxim, compound of formula (I)+bromoxynil, compound of formula (I)+butachlor, compound of formula (I)+butafenacil, compound of formula (I)+butamifos, compound of formula (I)+butralin, compound of formula (I)+butroxydim, compound of formula (I)+butylate, compound of formula (I)+cacodylic acid, compound of formula (I)+calcium chlorate, compound of formula (I)+cafenstrole, compound of formula (I)+carbetamide, compound of formula (I)+carfentrazone, compound of formula (I)+carfentrazone-ethyl, compound of formula (I)+CDEA, compound of formula (I)+CEPC, compound of formula (I)+chlorflurenol, compound of formula (I)+chlorflurenol-methyl, compound of formula (I)+chloridazon, compound of formula (I)+chlorimuron, compound of formula (I)+chlorimuron-ethyl, compound of formula (I)+chloroacetic acid, compound of formula (I)+chlorotoluron, compound of formula (I)+chlorpropham, compound of formula (I)+chlorsulfuron, compound of formula (I)+chlorthal, compound of formula (I)+chlorthal-dimethyl, compound of formula (I)+cinidon-ethyl, compound of formula (I)+cinmethylin, compound of formula (I)+cinosulfuron, compound of formula (I)+cisanilide, compound of formula (I)+clethodim, compound of formula (I)+clodinafop, compound of formula (I)+clodinafop-propargyl, compound of formula (I)+clomazone, compound of formula (I)+clomeprop, compound of formula (I)+clopyralid, compound of formula (I)+cloransulam, compound of formula (I)+cloransulam-methyl, compound of formula (I)+CMA, compound of formula (I)+4-CPB, compound of formula (I)+CPMF, compound of formula (I)+4-CPP, compound of formula (I)+CPPC, compound of formula (I)+cresol, compound of formula (I)+cumyluron, compound of formula (I)+cyanamide, compound of formula (I)+cyanazine, compound of formula (I)+cycloate, compound of formula (I)+cyclosulfamuron, compound of formula (I)+cycloxydim, compound of formula (I)+cyhalofop, compound of formula (I)+cyhalofop-butyl, compound of formula (I)+2,4-D, compound of formula (I)+3,4-DA, compound of formula (I)+daimuron, compound of formula (I)+dalapon, compound of formula (I)+dazomet, compound of formula (I)+2,4-DB, compound of formula (I)+3,4-DB, compound of formula (I)+2,4-DEB, compound of formula (I)+desmedipham, formula (I)+desmetryn, compound of formula (I)+dicamba, compound of formula (I)+dichlobenil, compound of formula (I)+ortho-dichlorobenzene, compound of formula (I)+para-dichlorobenzene, compound of formula (I)+dichlorprop, compound of formula (I)+dichlorprop-P, compound of formula (I)+diclofop, compound of formula (I)+diclofop-methyl, compound of formula (I)+diclosulam, compound of formula (I)+difenzoquat, compound of formula (I)+difenzoquat metilsulfate, compound of formula (I)+diflufenican, compound of formula (I)+diflufenzopyr, compound of formula (I)+dimefuron, compound of formula (I)+dimepiperate, compound of formula (I)+dimethachlor, compound of formula (I)+dimethametryn, compound of formula (I)+dimethenamid, compound of formula (I)+dimethenamid-P, compound of formula (I)+dimethipin, compound of formula (I)+dimethylarsinic acid, compound of formula (I)+dinitramine, compound of formula (I)+dinoterb, compound of formula (I)+diphenamid, formula (I)+dipropetryn, compound of formula (I)+diquat, compound of formula (I)+diquat dibromide, compound of formula (I)+dithiopyr, compound of formula (I)+diuron, compound of formula (I)+DNOC, compound of formula (I)+3,4-DP, compound of formula (I)+DSMA, compound of formula (I)+EBEP, compound of formula (I)+endothal, compound of formula (I)+EPTC, compound of formula (I)+esprocarb, compound of formula (I)+ethalfluralin, compound of formula (I)+ethametsulfuron, compound of formula (I)+ethametsulfuron-methyl, formula (I)+ethephon, compound of formula (I)+ethofumesate, compound of formula (I)+ethoxyfen, compound of formula (I)+ethoxysulfuron, compound of formula (I)+etobenzanid, compound of formual (I)+fenoxaprop, compound of formula (I)+fenoxaprop-P, compound of formula (I)+fenoxaprop-ethyl, compound of formula (I)+fenoxaprop-P-ethyl, compound of formula (I)+fentrazamide, compound of formula (I)+ferrous sulfate, compound of formula (I)+flamprop-M, compound of formula (I)+flazasulfuron, compound of formula (I)+florasulam, compound of formula (I)+fluazifop, compound of formula (I)+fluazifop-butyl, compound of formula (I)+fluazifop-P, compound of formula (I)+fluazifop-P-butyl, formula (I)+fluazolate, compound of formula (I)+flucarbazone, compound of formula (I)+flucarbazone-sodium, compound of formula (I)+flucetosulfuron, compound of formula (I)+fluchloralin, compound of formula (I)+flufenacet, compound of formula (I)+flufenpyr, compound of formula (I)+flufenpyr-ethyl, formula (I)+flumetralin, compound of formula (I)+flumetsulam, compound of formula (I)+flumiclorac, compound of formula (I)+flumiclorac-pentyl, compound of formula (I)+flumioxazin, formula (I)+flumipropin, compound of formula (I)+fluometuron, compound of formula (I)+fluoroglycofen, compound of formula (I)+fluoroglycofen-ethyl, formula (I)+fluoxaprop, formula (I)+flupoxam, formula (I)+flupropacil, compound of formula (I)+flupropanate, compound of formula (I)+flupyrsulfuron, compound of formula (I)+flupyrsulfuron-methyl-sodium, compound of formula (I)+flurenol, compound of formula (I)+fluridone, compound of formula (I)+flurochloridone, compound of formula (I)+fluroxypyr, compound of formula (I)+flurtamone, compound of formula (I)+fluthiacet, compound of formula (I)+fluthiacet-methyl, compound of formula (I)+fomesafen, compound of formula (I)+foramsulfuron, compound of formula (I)+fosamine, compound of formula (I)+glufosinate, compound of formula (I)+glufosinate-ammonium, compound of formula (I)+glyphosate, compound of formula (I)+halauxifen, compound of formula (I)+halauxifen-methyl, compound of formula (I)+halosulfuron, compound of formula (I)+halosulfuron-methyl, compound of formula (I)+haloxyfop, compound of formula (I)+haloxyfop-P, compound of formula (I)+HC-252, compound of formula (I)+hexazinone, compound of formula (I)+imazamethabenz, compound of formula (I)+imazamethabenz-methyl, compound of formula (I)+imazamox, compound of formula (I)+imazapic, compound of formula (I)+imazapyr, compound of formula (I)+imazaquin, compound of formula (I)+imazethapyr, compound of formula (I)+imazosulfuron, compound of formula (I)+indanofan, compound of formula (I) and indaziflam, compound of formula (I)+iodomethane, compound of formula (I)+iodosulfuron, compound of formula (I)+iodosulfuron-methyl-sodium, compound of formula (I)+ioxynil, compound of formula (I) and ipfencarbazone, compound of formula (I)+isoproturon, compound of formula (I)+isouron, compound of formula (I)+isoxaben, compound of formula (I)+isoxachlortole, compound of formula (I)+isoxaflutole, formula (I)+isoxapyrifop, compound of formula (I)+karbutilate, compound of formula (I)+lactofen, compound of formula (I)+lenacil, compound of formula (I)+linuron, compound of formula (I)+MAA, compound of formula (I)+MAMA, compound of formula (I)+MCPA, compound of formula (I)+MCPA-thioethyl, compound of formula (I)+MCPB, compound of formula (I)+mecoprop, compound of formula (I)+mecoprop-P, compound of formula (I)+mefenacet, compound of formula (I)+mefluidide, compound of formula (I)+mesosulfuron, compound of formula (I)+mesosulfuron-methyl, compound of formula (I)+mesotrione, compound of formula (I)+metam, compound of formula (I)+metamifop, compound of formula (I)+metamitron, compound of formula (I)+metazachlor, compound of formula (I) and metazosulfuron, compound of formula (I)+methabenzthiazuron, formula (I)+methazole, a compound of formula (I) and methiozolin, compound of formula (I)+methylarsonic acid, compound of formula (I)+methyldymron, compound of formula (I)+methyl isothiocyanate, compound of formula (I)+metobenzuron, formula (I)+metobromuron, compound of formula (I)+metolachlor, compound of formula (I)+S-metolachlor, compound of formula (I)+metosulam, compound of formula (I)+metoxuron, compound of formula (I)+metribuzin, compound of formula (I)+metsulfuron, compound of formula (I)+metsulfuron-methyl, compound of formula (I)+MK-616, compound of formula (I)+molinate, compound of formula (I)+monolinuron, a compound of formula (I) and monosulfuron, a compound of formula (I) and monosulfuron-ester compound of formula (I)+MSMA, compound of formula (I)+naproanilide, compound of formula (I)+napropamide, compound of formula (I)+naptalam, formula (I)+NDA-402989, compound of formula (I)+neburon, compound of formula (I)+nicosulfuron, formula (I)+nipyraclofen, formula (I)+n-methyl glyphosate, compound of formula (I)+nonanoic acid, compound of formula (I)+norflurazon, compound of formula (I)+oleic acid (fatty acids), compound of formula (I)+orbencarb, compound of formula (I)+orthosulfamuron, compound of formula (I)+oryzalin, compound of formula (I)+oxadiargyl, compound of formula (I)+oxadiazon, compound of formula (I)+oxasulfuron, compound of formula (I)+oxaziclomefone, compound of formula (I)+oxyfluorfen, compound of formula (I)+paraquat, compound of formula (I)+paraquat dichloride, compound of formula (I)+pebulate, compound of formula (I)+pendimethalin, compound of formula (I)+penoxsulam, compound of formula (I)+pentachlorophenol, compound of formula (I)+pentanochlor, compound of formula (I)+pentoxazone, compound of formula (I)+pethoxamid, compound of formula (I)+petrolium oils, compound of formula (I)+phenmedipham, compound of formula (I)+phenmedipham-ethyl, compound of formula (I)+picloram, compound of formula (I)+picolinafen, compound of formula (I)+pinoxaden, compound of formula (I)+piperophos, compound of formula (I)+potassium arsenite, compound of formula (I)+potassium azide, compound of formula (I)+pretilachlor, compound of formula (I)+primisulfuron, compound of formula (I)+primisulfuron-methyl, compound of formula (I)+prodiamine, compound of formula (I)+profluazol, compound of formula (I)+profoxydim, formula (I)+prohexadione-calcium, compound of formula (I)+prometon, compound of formula (I)+prometryn, compound of formula (I)+propachlor, compound of formula (I)+propanil, compound of formula (I)+propaquizafop, compound of formula (I)+propazine, compound of formula (I)+propham, compound of formula (I)+propisochlor, compound of formula (I)+propoxycarbazone, compound of formula (I)+propoxycarbazone-sodium, compound of formula (I)+propyzamide, compound of formula (I)+prosulfocarb, compound of formula (I)+prosulfuron, compound of formula (I)+pyraclonil, compound of formula (I)+pyraflufen, compound of formula (I)+pyraflufen-ethyl, formula (I)+pyrasulfotole, compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyributicarb, compound of formula (I)+pyridafol, compound of formula (I)+pyridate, compound of formula (I)+pyriftalid, compound of formula (I)+pyriminobac, compound of formula (I)+pyriminobac-methyl, compound of formula (I)+pyrimisulfan, compound of formula (I)+pyrithiobac, compound of formula (I)+pyrithiobac-sodium, formula (I)+pyroxasulfone, formula (I)+pyroxulam, compound of formula (I)+quinclorac, compound of formula (I)+quinmerac, compound of formula (I)+quinoclamine, compound of formula (I)+quizalofop, compound of formula (I)+quizalofop-P, compound of formula (I)+quizalofop-ethyl, compound of formula (I)+quizalofop-P-ethyl, compound of formula (I)+rimsulfuron, compound of formula (I)+saflufenacil, compound of formula (I)+sethoxydim, compound of formula (I)+siduron, compound of formula (I)+simazine, compound of formula (I)+simetryn, compound of formula (I)+SMA, compound of formula (I)+sodium arsenite, compound of formula (I)+sodium azide, compound of formula (I)+sodium chlorate, compound of formula (I)+sulcotrione, compound of formula (I)+sulfentrazone, compound of formula (I)+sulfometuron, compound of formula (I)+sulfometuron-methyl, compound of formula (I)+sulfosate, compound of formula (I)+sulfosulfuron, compound of formula (I)+sulfuric acid, compound of formula (I)+tar oils, compound of formula (I)+2,3,6-TBA, compound of formula (I)+TCA, compound of formula (I)+TCA-sodium, formula (I)+tebutam, compound of formula (I)+tebuthiuron, formula (I)+tefuryltrione, compound of formula 1+tembotrione, compound of formula (I)+tepraloxydim, compound of formula (I)+terbacil, compound of formula (I)+terbumeton, compound of formula (I)+terbuthylazine, compound of formula (I)+terbutryn, compound of formula (I)+thenylchlor, compound of formula (I)+thiazafluron, compound of formula (I)+thiazopyr, compound of formula (I)+thifensulfuron, compound of formula (I)+thiencarbazone, compound of formula (I)+thifensulfuron-methyl, compound of formula (I)+thiobencarb, compound of formula (I)+tiocarbazil, compound of formula (I)+topramezone, compound of formula (I)+tralkoxydim, a compound of formula (I) and triafamone compound of formula (I)+tri-allate, compound of formula (I)+triasulfuron, compound of formula (I)+triaziflam, compound of formula (I)+tribenuron, compound of formula (I)+tribenuron-methyl, compound of formula (I)+tricamba, compound of formula (I)+triclopyr, compound of formula (I)+trietazine, compound of formula (I)+trifloxysulfuron, compound of formula (I)+trifloxysulfuron-sodium, compound of formula (I)+trifluralin, compound of formula (I)+triflusulfuron, compound of formula (I)+triflusulfuron-methyl, compound of formula (I)+trifop, compound of formula (I)+trifop-methyl, compound of formula (I)+trihydroxytriazine, compound of formula (I)+trinexapac-ethyl, compound of formula (I)+tritosulfuron, compound of formula (I)+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula (I)+2-[[8-chloro-3,4-dihydro-4-(4-methoxyphenyl)-3-oxo-2-quinoxalinyl]carbonyl-1,3-cyclohexanedione and the compound of formula (I)+VX-573.

In particular, the following mixtures are important:
 mixtures of a compound of formula (I) with an acetanilide (e.g. compound of formula (I)+acetochlor, compound of formula (I)+dimethenamid, compound of formula (I)+metolachlor, compound of formula (I)+S-metolachlor, or compound of formula (I)+pretilachlor) or with other inhibitors of very long chain fatty acid esterases (VLCFAE) (e.g. compound of formula (I)+pyroxasulfone).
 mixtures of a compound of formula (I) with an HPPD inhibitor (e.g. compound of formula (I)+isoxaflutole, compound of formula (I)+mesotrione, compound of formula (I)+pyrasulfotole, compound of formula (I)+sulcotrione, compound of formula (I)+tembotrione, compound of formula (I)+topramezone, compound of formula (I)+bicyclopyrone;
 mixtures of a compound of formula (I) with a triazine (e.g. compound of formula (I)+atrazine, or compound of formula (I)+terbuthylazine);
 mixtures of a compound of formula (I) with glyphosate;
 mixtures of a compound of formula (I) with glufosinate-ammonium;
 mixtures of a compound of formula (I) with a PPO inhibitor (e.g. compound of formula (I)+acifluorfen-sodium, compound of formula (I)+butafenacil, compound of formula (I)+carfentrazone-ethyl, compound of formula (I)+cinidon-ethyl, compound of formula (I)+flumioxazin, compound of formula (I)+fomesafen, compound of formula (I)+lactofen, or compound of formula (I)+SYN 523 ([3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester) (CAS RN 353292-31-6)).

Whilst two-way mixtures of a compound of formula (I) and another herbicide are explicitly disclosed above, the skilled man will appreciate that the invention extends to three-way, and further multiple combinations comprising the above two-way mixtures. In particular, the invention extends to:
 mixtures of a compound of formula (I) with a triazine and an HPPD inhibitor (e.g. compound of formula (I)+triazine+isoxaflutole, compound of formula (I)+triazine+mesotrione, compound of formula (I)+triazine+pyrasulfotole, compound of formula (I)+triazine+sulcotrione, compound of formula (I)+triazine+tembotrione, compound of formula (I)+triazine+topramezone, compound of formula (I)+triazine+bicyclopyrone;
 mixtures of a compound of formula (I) with glyphosate and an HPPD inhibitor (e.g. compound of formula (I)+glyphosate+isoxaflutole, compound of formula (I)+glyphosate+mesotrione, compound of formula (I)+glyphosate+pyrasulfotole, compound of formula (I)+glyphosate+sulcotrione, compound of formula (I)+glyphosate+tembotrione, compound of formula (I)+glyphosate+topramezone, compound of formula (I)+glyphosate+bicyclopyrone;
 mixtures of a compound of formula (I) with glufosinate-ammonium and an HPPD inhibitor (e.g. compound of formula (I)+glufosinate-ammonium+isoxaflutole, compound of formula (I)+glufosinate-ammonium+mesotrione, compound of formula (I)+glufosinate-ammonium+pyrasulfotole, compound of formula (I)+glufosinate-ammonium+sulcotrione, compound of formula (I)+glufosinate-ammonium+tembotrione, compound of formula (I)+glufosinate-ammonium+topramezone, compound of formula (I)+glufosinate-ammonium+bicyclopyrone;
 mixtures of a compound of formula (I) with a VLCFAE inhibitor and an HPPD inhibitor (e.g. compound of formula (I)+S-metolachlor+isoxaflutole, compound of formula (I)+S-metolachlor+mesotrione, compound of formula (I)+S-metolachlor+pyrasulfotole, compound of formula (I)+S-metolachlor+sulcotrione, compound of formula (I)+S-metolachlor+tembotrione, compound of formula (I)+S-metolachlor+topramezone, compound of formula (I)+S-metolachlor+bicyclopyrone, compound of formula (I)+acetochlor+isoxaflutole, compound of formula (I)+acetochlor+mesotrione, compound of formula (I)+acetochlor+pyrasulfotole, compound of formula (I)+acetochlor+sulcotrione, compound of formula (I)+acetochlor+tembotrione, compound of formula (I)+acetochlor+topramezone, compound of formula (I)+acetochlor+bicyclopyrone, compound of formula (I)+pyroxasulfone+isoxaflutole, compound of formula (I)+pyroxasulfone+mesotrione, compound of formula (I)+pyroxasulfone+pyrasulfotole, compound of formula (I)+pyroxasulfone+sulcotrione, compound of formula (I)+pyroxasulfone+tembotrione, compound of formula (I)+pyroxasulfone+topramezone, compound of formula (I)+pyroxasulfone+bicyclopyrone.

Particularly preferred are mixtures of the compound of formula (I) with mesotrione, bicyclopyrone, isoxaflutole, tembotrione, topramezone, sulcotrione, pyrasulfotole, metolachlor, S-metolachlor, acetochlor, pyroxasulfone, P-dimethenamid, dimethenamid, flufenacet, pethoxamid, atrazine, terbuthylazine, bromoxynil, metribuzin, amicarbazone, bentazone, ametryn, hexazinone, diuron, tebuthiuron, glyphosate, paraquat, diquat, glufosinate, acifluorfen-sodium, butafenacil, carfentrazone-ethyl, cinidon-ethyl, flumioxazin, fomesafen, lactofen, [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester.

The mixing partners of the compound of formula (I) may also be in the form of esters or salts, as mentioned e.g. in The Pesticide Manual, 14th Edition (BCPC), 2006. The reference to acifluorfen-sodium also applies to acifluorfen, the reference to dimethenamid also applies to dimethenamid-P, the reference to glufosinate-ammonium also applies to glufosinate, the reference to bensulfuron-methyl also applies to bensulfuron, the reference to cloransulam-methyl also applies to cloransulam, the reference to flamprop-M also applies to flamprop, and the reference to pyrithiobac-sodium also applies to pyrithiobac, etc.

The mixing ratio of the compound of formula (I) to the mixing partner is preferably from 1:100 to 1000:1.

The mixtures can advantageously be used in the above-mentioned formulations (in which case "active ingredient" relates to the respective mixture of compound of formula (I) with the mixing partner).

The compounds of formula (I) according to the invention can also be used in combination with one or more safeners. Likewise, mixtures of a compound of formula (I) according to the invention with one or more further active ingredients, in particular with one or more further herbicides, can also be used in combination with one or more safeners. The term "safener" as used herein means a chemical that when used in combination with a herbicide reduces the undesirable effects of the herbicide on non-target organisms, for example, a safener protects crops from injury by herbicides but does not prevent the herbicide from killing the weeds. Where a compound of formula (I) is combined with a safener, the following combinations of the compound of formula (I) and the safener are particularly preferred. Compound of formula (I)+AD 67 (MON 4660), compound of formula (I)+benoxacor, compound of formula (I)+cloquintocet-mexyl, compound of formula (I)+cyometrinil and a compound of formula (I)+the corresponding (Z) isomer of cyometrinil, compound of formula (I)+cyprosulfamide (CAS RN 221667-31-8), compound of formula (I)+dichlormid, compound of formula (I) and dicyclonon, compound of formula (I) and dietholate, compound of formula (I)+fenchlorazole-ethyl, compound of formula (I)+fenclorim, compound of formula (I)+flurazole, compound of formula (I)+fluxofenim, compound of formula (I)+furilazole and a compound of formula (I)+the corresponding R isomer or furilazome, compound of formula (I)+isoxadifen-ethyl, compound of formula (I)+mefenpyr-diethyl, compound of formula (I) and mephenate, compound of formula (I)+oxabetrinil, compound of formula (I)+naphthalic anhydride (CAS RN 81-84-5), compound of formula (I) and TI-35, compound of formula (I)+N-isopropyl-4-(2-methoxy-benzoylsulfamoyl)-benzamide (CAS RN 221668-34-4) and a compound of formula (I)+N-(2-methoxybenzoyl)-4-[(methylaminocarbonyl)amino]benzenesulfonamide. Particularly preferred are mixtures of a compound of formula (I) with benoxacor, a compound of formula (I) with cloquintocet-mexyl, a compound of formula (I)+cyprosulfamide and a compound of formula (I) with N-(2-methoxybenzoyl)-4-[(methylaminocarbonyl)amino]benzenesulfonamide.

The safeners of the compound of formula (I) may also be in the form of esters or salts, as mentioned e.g. in The Pesticide Manual, 14th Edition (BCPC), 2006. The reference to cloquintocet-mexyl also applies to cloquintocet and to a lithium, sodium, potassium, calcium, magnesium, aluminium, iron, ammonium, quaternary ammonium, sulfonium or phosphonium salt thereof as disclosed in WO02/34048 and the reference to fenchlorazole-ethyl also applies to fenchlorazole, etc.

Preferably the mixing ratio of compound of formula (I) to safener is from 100:1 to 1:10, especially from 20:1 to 1:1.

The mixtures can advantageously be used in the above-mentioned formulations (in which case "active ingredient" relates to the respective mixture of compound of formula (I) and any further active ingredient, in particular a further herbicide, with the safener).

It is possible that the safener and a compound of formula (I) and one or more additional herbicide(s), if any, are applied simultaneously. For example, the safener, a compound of formula (I) and one or more additional herbicide(s), if any, might be applied to the locus pre-emergence or might be applied to the crop post-emergence. It is also possible that the safener and a compound of formula (I) and one or more additional herbicide(s), if any, are applied sequentially. For example, the safener might be applied before sowing the seeds as a seed treatment and a compound of formula (I) and one or more additional herbicides, if any, might be applied to the locus pre-emergence or might be applied to the crop post-emergence.

Preferred mixtures of a compound of formula (I) with further herbicides and safeners include:

Mixtures of a compound of formula (I) with S-metolachlor and a safener, particularly benoxacor.

Mixtures of a compound of formula (I) with isoxaflutole and a safener.

Mixtures of a compound of formula (I) with mesotrione and a safener.

Mixtures of a compound of formula (I) with sulcotrione and a safener.

Mixtures of a compound of formula (I) with tembotrione and a safener.

Mixtures of a compound of formula (I) with topramezone and a safener.

Mixtures of a compound of formula (I) with bicyclopyrone and a safener.

Mixtures of a compound of formula (I) with a triazine and a safener.

Mixtures of a compound of formula (I) with a triazine and isoxaflutole and a safener.

Mixtures of a compound of formula (I) with a triazine and mesotrione and a safener.

Mixtures of a compound of formula (I) with a triazine and sulcotrione and a safener.

Mixtures of a compound of formula (I) with a triazine and tembotrione and a safener.

Mixtures of a compound of formula (I) with a triazine and topramezone and a safener.

Mixtures of a compound of formula (I) with a triazine and bicyclopyrone and a safener.

Mixtures of a compound of formula (I) with glyphosate and a safener.

Mixtures of a compound of formula (I) with glyphosate and isoxaflutole and a safener.

Mixtures of a compound of formula (I) with glyphosate and mesotrione and a safener.

Mixtures of a compound of formula (I) with glyphosate and sulcotrione and a safener.

Mixtures of a compound of formula (I) with glyphosate and tembotrione and a safener.

Mixtures of a compound of formula (I) with glyphosate and topramezone and a safener.

Mixtures of a compound of formula (I) with glyphosate and bicyclopyrone and a safener.

Mixtures of a compound of formula (I) with glufosinate-ammonium and a safener.

Mixtures of a compound of formula (I) with glufosinate-ammonium and isoxaflutole and a safener.

Mixtures of a compound of formula (I) with glufosinate-ammonium and mesotrione and a safener.

Mixtures of a compound of formula (I) with glufosinate-ammonium and sulcotrione and a safener.

Mixtures of a compound of formula (I) with glufosinate-ammonium and tembotrione and a safener.

Mixtures of a compound of formula (I) with glufosinate-ammonium and topramezone and a safener.

Mixtures of a compound of formula (I) with glufosinate-ammonium and bicyclopyrone and a safener.

Mixtures of a compound of formula (I) with S-metolachlor and a safener.

Mixtures of a compound of formula (I) with S-metolachlor and isoxaflutole and a safener.

Mixtures of a compound of formula (I) with S-metolachlor and mesotrione and a safener.

Mixtures of a compound of formula (I) with S-metolachlor and sulcotrione and a safener.

Mixtures of a compound of formula (I) with S-metolachlor and tembotrione and a safener.

Mixtures of a compound of formula (I) with S-metolachlor and topramezone and a safener.

Mixtures of a compound of formula (I) with S-metolachlor and bicyclopyrone and a safener Mixtures of a compound of formula (I) with pyroxasulfone and a safener.

Mixtures of a compound of formula (I) with pyroxasulfone and isoxaflutole and a safener.

Mixtures of a compound of formula (I) with pyroxasulfone and mesotrione and a safener.

Mixtures of a compound of formula (I) with pyroxasulfone and sulcotrione and a safener.

Mixtures of a compound of formula (I) with pyroxasulfone and tembotrione and a safener.

Mixtures of a compound of formula (I) with pyroxasulfone and topramezone and a safener.

Mixtures of a compound of formula (I) with pyroxasulfone and bicyclopyrone and a safener Mixtures of a compound of formula (I) with acetochlor and a safener.

Mixtures of a compound of formula (I) with acetochlor and isoxaflutole and a safener.

Mixtures of a compound of formula (I) with acetochlor and mesotrione and a safener.

Mixtures of a compound of formula (I) with acetochlor and sulcotrione and a safener.

Mixtures of a compound of formula (I) with acetochlor and tembotrione and a safener.

Mixtures of a compound of formula (I) with acetochlor and topramezone and a safener.

Mixtures of a compound of formula (I) with acetochlor and bicyclopyrone and a safener Various aspects and embodiments of the present invention will now be illustrated in more detail by way of example. It will be appreciated that modification of detail may be made without departing from the scope of the invention.

For the avoidance of doubt, where a literary reference, patent application, or patent, is cited within the text of this application, the entire text of said citation is herein incorporated by reference.

EXAMPLES

Preparation Examples

The following abbreviations were used in this section: s=singlet; bs=broad singlet; d=doublet; dd=double doublet; dt=double triplet; t=triplet, tt=triple triplet, q=quartet, sept=septet; m=multiplet; RT=retention time, $MH^+$=molecular mass of the molecular cation.

1H NMR spectra were recorded at 400 MHz either on a Varian Unity Inova instrument or Bruker AVANCE-II instrument.

Where $R_2$ is not H, the compounds may exist in a mixture of diastereoisomers, which may be observed by LC-MS and NMR. The stereochemistry of the chiral centre at the carbon containing the $R_3$ group was generally found to interconvert at room temperature. Depending on the nature of $R_2$ substitution and the conditions for product synthesis, purification and analysis the ratio of diastereromers may change.

Example 1

Preparation of 3-(6-tert-butylpyrimidin-4-yl)-4-hydroxy-1-methyl-imidazolidin-2-one (A1)

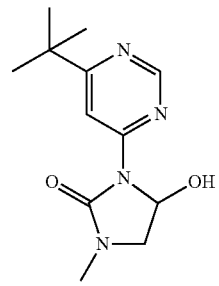 [SMILES: CN1CC(O)N(c2cc(C(C)(C)C)ncn2)C1=O]

Procedure for Synthesis of
1-(2,2-dimethoxyethyl)-1-methyl-urea (Step-1)

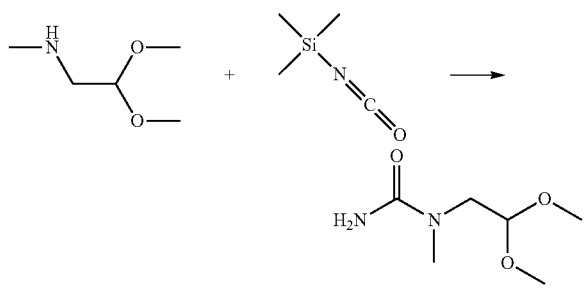

A solution of (methylamino)acetaldehyde dimethyl acetal ((commercially available) (20 g, 0.167 mol) in DCM (46 mL) was treated with trimethylsilyl isocyanate (commercially available) (46 mL, 335 mmol) over 15 mins, keeping internal temperature below 25° C. The reaction was then left to stir at room temperature for 8 days. Reaction was evaporated at reduced pressure (100 to 1 mBar with liquid $N_2$ trap at 20 to 40° C.) to give a white solid/gum mix, which was dissolved in 100 ml water. After 22 h, was evaporated at reduced pressure (1 mbar at 30-40° C.) and left dry for 8 h under these conditions to give product as a tacky white solid mass (26.0 g, 95% yield).

$^1$H NMR (CDCl$_3$): 4.80 (br s, 2H), 4.45 (t, 1H), 3.44 (s, 6H), 3.36 (d, 2H), 2.96 (s, 3H).

Procedure for Synthesis of 3-(6-tert-butylpyrimidin-4-yl)-1-(2,2-dimethoxyethyl)-1-methyl-urea (Step-2)

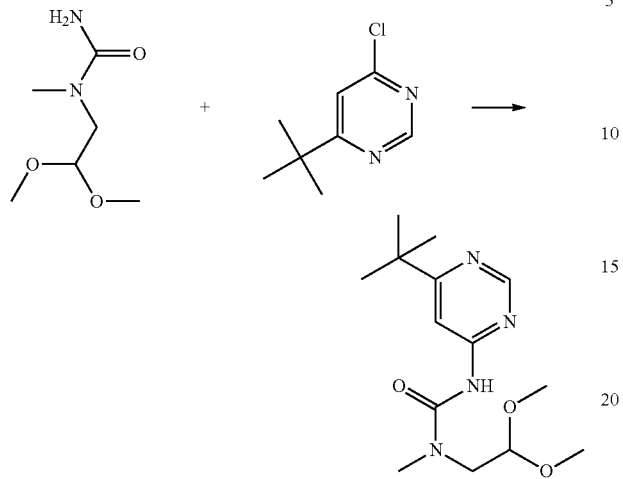

A solution of 1-(2,2-dimethoxyethyl)-1-methyl-urea ((243 mg, 1.50 mmol), 4-tert-butyl-6-chloro-pyrimidine (for a synthesis see WO 2011045353) (256 mg, 1.50 mmol), tris(dibenzylideneacetone)dipalladium(0) (34.3 mg, 0.0375 mmol) and 4,5-bis(diphenylphosphino)-9,9-dimethylxanthene (89.5 mg, 0.150 mmol), in 1,4-dioxane (7.5 mL) was added Cs₂CO₃ (733 mg, 2.25 mmol) under a Nitrogen atmosphere and the reaction was then heated at 90° C. for 65 minutes in a sealed vial. The mixture was allowed to cool to room temperature, filtered then chromatographed on silica eluting with 10-85% EtOAc in isohexane. Fractions containing product were evaporated to give desired product as an amber gum which was without further purification in the next reaction.

¹HNMR (CDCl₃): 8.74 (s, 1H), 7.98 (s, 1H), 4.52 (t, 1H), 3.52 (s, 6H), 3.47 (d, 2H), 3.09 (s, 3H), 1.34 (s, 9H).

Procedure for Synthesis of 3-(6-tert-butylpyrimidin-4-yl)-4-hydroxy-1-methyl-imidazolidin-2-one (Step-3)

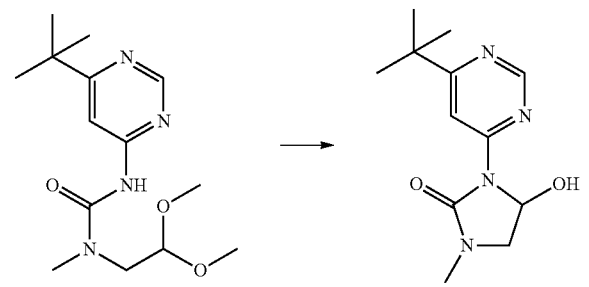 [SMILES: COC(CN(C)C(=O)Nc1cc(C(C)(C)C)ncn1)OC ; CN1CC(O)N(c2cc(C(C)(C)C)ncn2)C1=O]

A solution of 3-(6-tert-butylpyrimidin-4-yl)-1-(2,2-dimethoxyethyl)-1-methyl-urea (213 mg, 0.719 mmol) in acetic acid (2 mL) was treated with water (2 mL) and then heated to 100° C. After 50 minutes, the reaction mixture was evaporated and azeotroped with 5 ml toluene. The amber gum residue was chromatographed on silica (eluting with with 30-55% EtOAc in isohexane. Fractions containing product were evaporated to give the desired product as an amber gum.

¹H NMR (CDCl₃): 8.77 (s, 1H), 8.24 (s, 1H), 6.07 (m, 1H), 5.00 (br s, 1H), 3.71 (dd, 1H), 3.40 (dd, 1H), 2.95 (s, 3H), 1.36 (s, 9H).

LC-MS: (positive ES MH+251).

Example 2 and 3

Preparation of 1-(6-tert-butylpyrimidin-4-yl)-4,5-dihydroxy-3-methyl-imidazolidin-2-one (A4) and 1-(6-tert-butylpyrimidin-4-yl)-4-ethoxy-5-hydroxy-3-methyl-imidazolidin-2-one (A5)

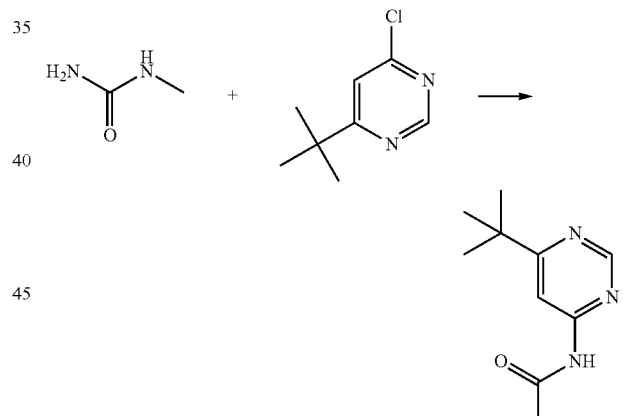

Procedure for Synthesis of 1-(6-tert-butylpyrimidin-4-yl)-3-methyl-urea (Step-1)

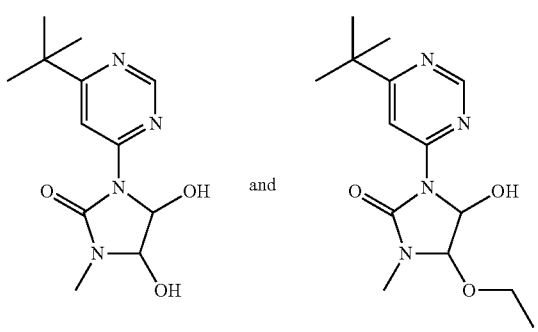 [SMILES: CN1C(=O)N(c2cc(C(C)(C)C)ncn2)C(O)C1O ; CCOC1C(O)N(c2cc(C(C)(C)C)ncn2)C(=O)N1C]

A mixture of tris(dibenzylideneacetone)dipalladium(0) (0.0859 g, 0.0938 mmol), 4,5-bis(diphenylphosphino)-9,9-dimethylxanthene (0.210 g, 0.352 mmol), potassium carbonate (0.822 g, 5.86 mmol) and methylurea (0.174 g, 2.34 mmol) in 1,4-dioxane (15 mL) was treated with 4-tert-butyl-6-chloro-pyrimidine (for a synthesis see WO 2011045353) (0.400 g, 2.34 mmol). The mixture was warmed to 75-80° C. with stirring under a N₂ atmosphere for 3 h. The reaction mixture was diluted with EtOAc (20 ml) and water (10 mL) and filtered through a pad of celite, rinsing through with further small portions of EtOAc and water. The organic phase was separated and the aqueous further extracted with EtOAc (5 mL). The organic extracts were combined, washed with brine (10 mL), dried over MgSO₄, filtered and the filtrate evaporated giving an orange liquid. This was chromatographed (eluting with an EtOAc/iso-hexane gradient) and fractions containing product were evaporated to give the desired product as a light yellow powder (0.178 g, 36%).

¹H NMR (CDCl₃): 9.08 (br.s, 1H), 8.92 (br.s, 1H), 8.71 (s, 1H), 6.79 (s, 1H), 2.97 (d, 3H), 1.33 (s, 9H).

Procedure for Synthesis of 1-(6-tert-butylpyrimidin-4-yl)-4,5-dihydroxy-3-methyl-imidazolidin-2-one (A4) (Step-2)

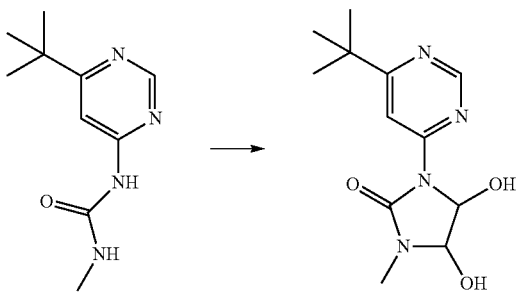 [SMILES: CNC(=O)Nc1cc(C(C)(C)C)ncn1 ; CN1C(=O)N(c2cc(C(C)(C)C)ncn2)C(O)C1O]

To 1-(6-tert-butylpyrimidin-4-yl)-3-methyl-urea (0.170 g, 0.816 mmol) in ethanol (5 mL) was added glyoxal (40% aqueous solution) (0.711 g, 4.90 mmol, 0.562 mL). The mixture was then heated at reflux for 2 h. The pale yellow reaction mixture was allowed to cool and stand at room temperature overnight. The reaction mixture was concentrated in vacuo and the residue was treated with DCM (20 mL) and washed with water (2×5 mL). The organic phase was dried over MgSO₄, filtered and the filtrate concentrated giving the crude product as a yellow oil. This was chromatographed (eluting with with an EtOAc/iso-hexane gradient) and fractions containing product were evaporated and dried under high vacuum to give the desired product as a white foam (140 mg, 64%). ¹H NMR indicated approximately a 3:1 ratio of diastereoisomers.

Major diastereoisomer: ¹H NMR (CDCl₃): 8.69 (d, 1H), 8.14 (d, 1H), 5.71 (s, 1H), 4.98 (s, 1H), 2.99 (s, 3H), 1.34 (s, 9H).

Minor diastereoisomer: ¹H NMR (CDCl₃): 8.75 (d, 1H), 8.21 (d, 1H), 5.92 (d, 1H), 5.13 (d, 1H), 2.96 (s, 3H), 1.34 (s, 9H).

LC-MS: (positive ES MH+267).

Procedure for synthesis of 1-(6-tert-butylpyrimidin-4-yl)-4-ethoxy-5-hydroxy-3-methyl-imidazolidin-2-one (A5) (Step-3)

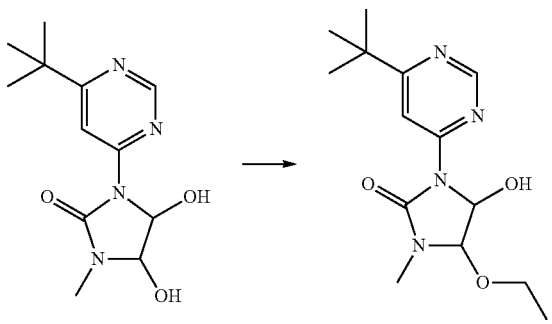 [SMILES: CN1C(=O)N(c2cc(C(C)(C)C)ncn2)C(O)C1O ; CCOC1C(O)N(c2cc(C(C)(C)C)ncn2)C(=O)N1C]

To a solution of 1-(6-tert-butylpyrimidin-4-yl)-4,5-dihydroxy-3-methyl-imidazolidin-2-one (0.120 g, 0.451 mmol) in ethanol (2 mL) was added conc sulfuric acid (0.05 mL) and the mixture was heated at reflux for 1 h. The reaction mixture was allowed to cool, and was evaporated in vacuo to give a pale yellow oil. The oil was treated with DCM (15 mL) and washed with water (2×3 mL), the organic phase dried over MgSO₄, filtered and the filtrate concentrated giving a cloudy, colourless gum. This was chromatographed (eluting with with an EtOAc/iso-hexane gradient) and fractions containing product were evaporated to give the desired product (17 mg, 13%), which NMR nOe experiments indicated was the trans diastereoisomer.

¹H NMR (CDCl₃): 8.76 (d, 1H), 8.16 (d, 1H), 5.72 (d, 1H), 4.80 (d, 1H), 4.70 (s, 1H), 3.65 (ddq, 2H), 2.99 (s, 3H), 1.34 (s, 9H), 1.27 (t, 3H).

LC-MS: (positive ES MH+295).

Example 4

1-(6-tert-butylpyrimidin-4-yl)-5-hydroxy-3-methoxy-4-methyl-imidazolidin-2-one (A6)

Procedure for synthesis of N,1,1-trimethoxypropan-2-imine (Step-1)

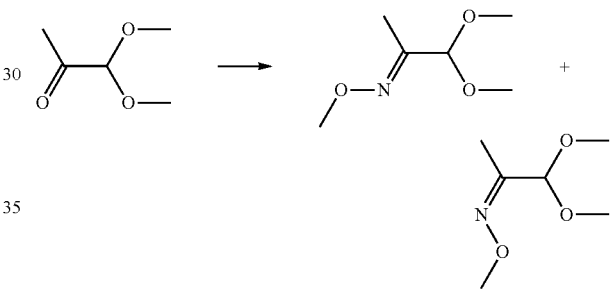

Methoxylamine hydrochloride (21.2 g) was suspended in methanol (65 mL) then potassium acetate (50.4 g, quickly ground in pestle and mortar to break up lumps) was added all at once and the thick white suspension resulting was stirred at room temp for 15 mins then cooled to 15° C. and then 1,1-dimethoxypropan-2-one (30 g) was added slowly over 25 mins. The reaction was stirred at room temperature for 50 mins and then diluted with 200 ml DCM, then 100 ml sat. NaHCO₃(aq) was added cautiously over 15 mins. After effervescence subsided, the layers were separated, extracted a further 2×80 ml DCM, dried Na₂SO₄, filtered and concentrated at 220 mbar and 35° C. (care as desired product is volatile) to give 37 g amber liquid, which was used without further purification.

1H NMR (CDCl₃) showed a 3:1 ratio of E:Z isomers

Procedure for Synthesis of N,1,1-trimethoxypropan-2-amine (Step-2)

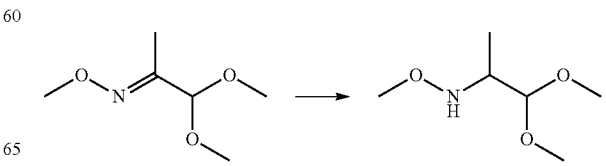

N,1,1-trimethoxypropan-2-imine (20 g) was dissolved in acetic acid (80 mL) then was cooled to 13° C. NaBH₃CN (9.82 g) was added portionwise over 10 mins. After 18 hrs at rt, reaction was concentrated to remove bulk of HOAc then residue dissolved in DCM (300 mL) and satd. NaHCO₃ (aq) (300 mL) was added slowly with stirring. The mixture was stirred at rt for 90 mins, and then 40% NaOH(aq) was added until the solution reached pH 12. The layers were separated, extracted with further DCM (3×100 ml). The combined DCM layers were dried (Na₂SO₄), filtered and evaporated to give 16.4 g of crude product as a pale amber oil, which was further purified by Kugelrohr distillation (120° C. at 70 mBar) to give product (12.0 g, 59% yield) which was approximately 95% pure by NMR and used without further purification.

Procedure for synthesis of 1-(2,2-dimethoxy-1-methyl-ethyl)-1-methoxy-urea (Step-3)

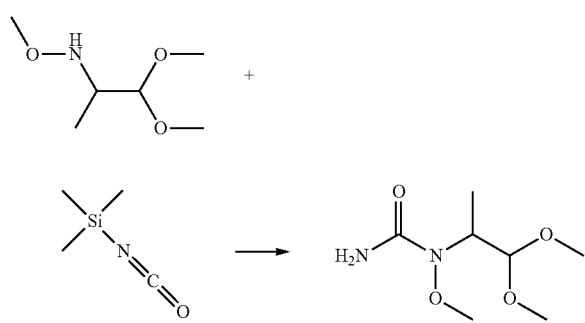

N,1,1-trimethoxypropan-2-amine (2.000 g, 13.41 mmol) was dissolved in IPA (5 ml) and the mixture was cooled to 0° C. under N₂, then trimethylsilyl isocyanate (commercially available) (4.83 mL 33.51 mmol) was added and the reaction was allowed to warm to rt and was stirred at room temp for 24 h. The reaction mixture was worked up by adding DCM (30 mL) and water (15 mL), extracting with further DCM (2×15 mL), dried (Na₂SO₄), filtered and evaporated to give product as a white solid (1 g, 39% yield).

¹H NMR (CDCl₃): 5.36 (br s, 2H), 4.47 (d, 1H), 4.32 (pentet, 1H), 3.75 (s, 3H), 3.37 (d, 6H), 1.24 (d, 3H).

Procedure for Synthesis of 3-(6-tert-butylpyrimidin-4-yl)-1-(2,2-dimethoxy-1-methyl-ethyl)-1-methoxy-urea (Step-4)

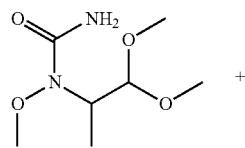

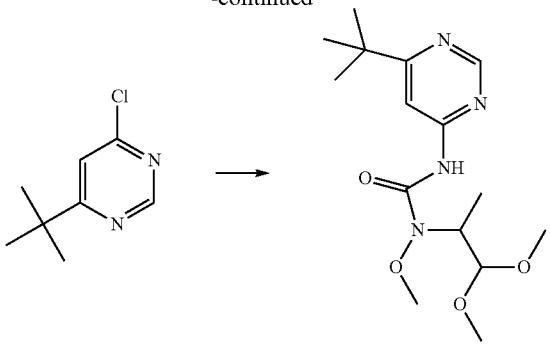

1-(2,2-dimethoxy-1-methyl-ethyl)-1-methoxy-urea (150 mg, 0.780 mmol), 4-tert-butyl-6-chloro-pyrimidine (for a synthesis see WO 2011045353) (160 mg), potassium carbonate (162 mg), tris(dibenzylideneacetone)dipalladium(0) (15 mg), 4,5-bis(diphenylphosphino)-9,9-dimethylxanthene (35 mg) were were suspended in 1-4-dioxane (1.5 mL) and the mixture was then heated at 110° C. in a sealed vial for 40 mins. Further 1-(2,2-dimethoxy-1-methyl-ethyl)-1-methoxy-urea (30 mg), tris(dibenzylideneacetone)dipalladium(0) (15 mg) and 4,5-bis(diphenylphosphino)-9,9-dimethylxanthene (35 mg) was added and the the mixture was then heated at 110° C. in a sealed vial for a further 50 mins. The mixture was allowed to cool to room temperature, diluted with 6 ml EtOAc, filtered then chromatographed on silica eluting with 0-100% EtOAc in isohexane. Fractions containing product were evaporated to give the desired product as a colourless gum (60 mg).

¹H NMR (CDCl₃): 8.77 (s, 1H), 8.35 (br s, 1H), 8.15 (s, 1H), 4.50 (d, 1H), 4.40 (pentet, 1H), 3.83 (s, 3H), 3.39 (d, 6H), 1.36 (s, 9H), 1.32 (d, 3H).

Procedure for Synthesis of 1-(6-tert-butylpyrimidin-4-yl)-5-hydroxy-3-methoxy-4-methyl-imidazolidin-2-one (Step-5)

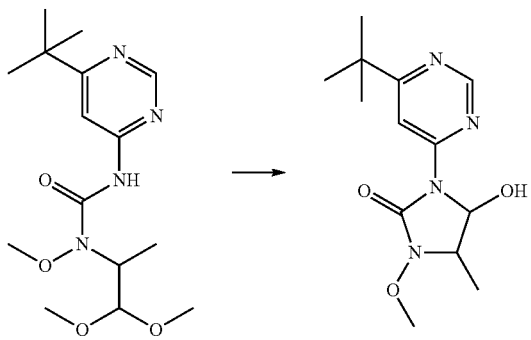 [SMILES: COC(OC)C(C)N(OC)C(=O)Nc1cc(C(C)(C)C)ncn1 ; CON1C(=O)N(c2cc(C(C)(C)C)ncn2)C(O)C1C]

3-(6-tert-butylpyrimidin-4-yl)-1-(2,2-dimethoxy-1-methyl-ethyl)-1-methoxy-urea (45 mg) was dissolved in acetic acid (1 mL) and water (0.5 mL) and stirred at room temperature for 25 mins and then at 60° C. for 20 mins and at at 85° C. for 20 mins. The reaction was left at room temperature for 3 days before heating again at 80° C. for 140 minutes. Reaction mixture was evaporated and then chromatographed on silica eluting with 0-85% EtOAc in isohexane. Fractions containing product were evaporated to give the desired product as a colourless gum (24 mg).

NMR indicated a ratio of diastereoisomers in approximately a 2:1 ratio.

Major diastereoisomer: ¹H NMR (CDCl₃) 8.79 (d, 1H), 8.24 (s, 1H), 5.53 (d, 1H), 5.10 (very br s, 1H), 3.90 (s, 3H), 3.70 (m, 1H), 1.44 (d, 3H), 1.35 (s, 9H).

Minor diastereoisomer: ¹H NMR (CDCl₃) 8.82 (d, 1H), 8.24 (s, 1H), 5.87 (d, 1H), 4.60 (very br s, 1H), 3.93 (s, 3H), 3.79 (m, 1H), 1.48 (d, 3H), 1.35 (s, 9H).

LC-MS: (positive ES MH+281).

Example 5

(A12), (A13), (A14) and (A15)

A sample of compound A3 was separated into four isomers (isomers 1, 2, 3 and 4) by preparative chiral HPLC (CHIRALPAK IC column, eluting with isoHexane (containing 0.1% TFA) and IPA. The first eluting isomer (isomer 1) and the third eluting isomer (isomer 3) were each found to equilibrate in solution to each give a mixture of isomers 1 and 3 overnight. The second eluting isomer (isomer 2) and the fourth eluting isomer (isomer 4) were each found to equilibrate in solution to each give a mixture of isomers 2 and 4 overnight.

A synthesis from ethyl (2S)-2-(methylamino)propanoate (see Example 6 below) showed that isomers 2 and 4 were of (S)-configuration at the four position of the dihydro-hydantoin ring. Similarly, it could be shown that isomers 1 and 3 were of (R)-configuration at the four position of the dihydro-hydantoin ring.

The absolute configuration could also be proven by X-ray crystallography.

Example A12/13 is therefore a readily interconverting mixture of (4R,5S)-1-(6-tert-butylpyrimidin-4-yl)-5-hydroxy-3,4-dimethyl-imidazolidin-2-one and (4R,5R)-1-(6-tert-butylpyrimidin-4-yl)-5-hydroxy-3,4-dimethyl-imidazolidin-2-one.

Example A14/15 is therefore a readily interconverting mixture of (4S,5S)-1-(6-tert-butylpyrimidin-4-yl)-5-hydroxy-3,4-dimethyl-imidazolidin-2-one and (4S,5R)-1-(6-tert-butylpyrimidin-4-yl)-5-hydroxy-3,4-dimethyl-imidazolidin-2-one.

Example 6

(4S,5S)-1-(6-tert-butylpyrimidin-4-yl)-5-hydroxy-3,4-dimethyl-imidazolidin-2-one and (4S,5R)-1-(6-tert-butylpyrimidin-4-yl)-5-hydroxy-3,4-dimethyl-imidazolidin-2-one A14 and A15, alternative synthesis Procedure for Synthesis of 6-tert-butylpyrimidin-4-amine (Step-1)

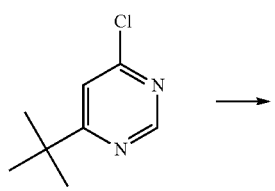

4-tert-butyl-6-chloro-pyrimidine (for a synthesis see WO 2011045353) (20 g, 117.204 mmol) and saturated aqueous ammonia (75 mL) were sealed in a pressure tube and heated at 100° C. for 18 h. The reaction was cooled and the solid filtered off. More solid was removed from tube by washing with methanol and then evaporating to give further crude product. The combined crude product was washed with water and dried to give the desired product as a white solid, (16.1 g (77%).

LC-MS: (positive ES MH+152).

Procedure for Synthesis of phenyl N-(6-tert-butylpyrimidin-4-yl)carbamate (Step 2)

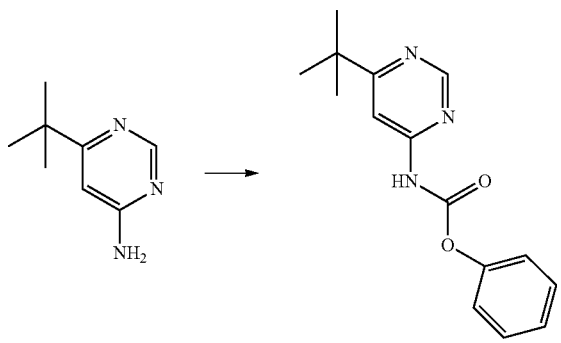 [SMILES: CC(C)(C)c1cc(N)ncn1 ; CC(C)(C)c1cc(NC(=O)Oc2ccccc2)ncn1]

6-tert-butylpyrimidin-4-amine (900 mg, 5.952 mmol) in DCM was treated with N-ethyl-N-isopropyl-propan-2-amine (1.14 mL, 16.547 mmol). The reaction was cooled with an ice bath to 0° C. and phenyl carbonochloridate (0.747 mL, 5.952 mmol) was added in portions over 30 min. keeping reaction temperature<5° C. Cooling was removed and reaction was stirred at room temperature overnight. The reaction was cooled to 0° C. again and further N-ethyl-N-isopropyl-propan-2-amine (300 μL) and phenyl carbonochloridate (200 μL) were added and reaction was stirred at room temperature for a further 30 mins. The reaction cooled to 0° C. again and further N-ethyl-N-isopropyl-propan-2-amine (150 μL) and phenyl carbonochloridate (100 μL) were added and reaction was stirred at room temperature for a further 30 mins. The reaction solution was then washed twice with aq citric acid, twice with sodium hydrogen carbonate soln, dried (MgSO₄) and evaporated. The residue was chromatographed (eluting with with an EtOAc/isohexane gradient) and fractions containing product were evaporated to give desired product (580 mg).

LC-MS: (positive ES MH+272).

Procedure for Synthesis of (5S)-3-(6-tert-butylpyrimidin-4-yl)-1,5-dimethyl-imidazolidine-2,4-dione (Step 3)

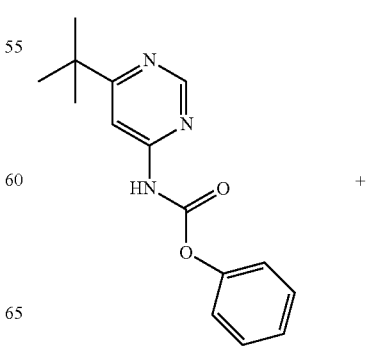

+

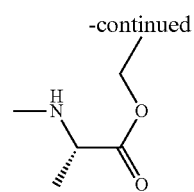

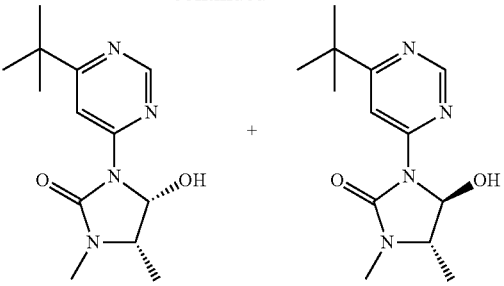

(5S)-3-(6-tert-butylpyrimidin-4-yl)-1,5-dimethyl-imidazolidine-2,4-dione (85 mg, 0.324 mmol) was stirred in methanol (5 mL) and was cooled on an ice bath. Sodium borohydride (12.5 mg, 0.324 mmol, 1 equiv.) was added in a single portion and the reaction was stirred for 2 h. Further sodium borohydride (12.5 mg, 0.324 mmol, 1 equiv.) was added and the reaction was stirred for 45 mins and then the reaction was treated with aq. citric acid solution and extracted with DCM. The combined organics were washed with water, dried (MgSO$_4$) and evaporated to give residue which was then chromatographed on silica eluting with EtOAc in isohexane. Fractions containing product were evaporated to give the desired product (36 mg, 0.136 mmol, 42%) in an approximate 2:1 trans:cis ratio by $^1$H NMR.

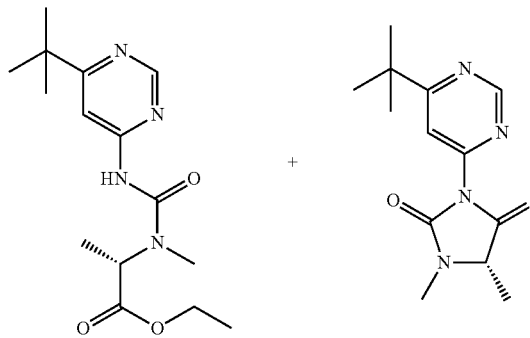

Phenyl N-(6-tert-butylpyrimidin-4-yl)carbamate (207 mg, 0.7623 mmol) and ethyl (2S)-2-(methylamino)propanoate (for a similar preparation see Tetrahedron Letters 1997, pages 5085-5086), (100 mg, 0.762 mmol) were stirred at room temperature in DMSO (1 mL) for 2 h. The reaction mixture was poured into water and was extracted with DCM. Extracts were washed with water, dried (MgSO$_4$) and evaporated to give residue which was then chromatographed on silica eluting with EtOAc in isohexane. Fractions containing product were evaporated to give the desired product as a colourless gum (96 mg, 48%).

LC-MS: (positive ES MH+263).

Uncyclised intermediate ethyl (2S)-2-[(6-tert-butylpyrimidin-4-yl)carbamoyl-methylamino]propanoate was also observed. LC-MS: (positive ES MH+309). The reaction may be heated to 80° C. for 8 h to convert ethyl (2S)-2-[(6-tert-butylpyrimidin-4-yl)carbamoyl-methylamino]propanoate to the desired product.

Procedure for Synthesis of (4S,5S)-1-(6-tert-butylpyrimidin-4-yl)-5-hydroxy-3,4-dimethyl-imidazolidin-2-one and (4S,5R)-1-(6-tert-butylpyrimidin-4-yl)-5-hydroxy-3,4-dimethyl-imidazolidin-2-one.
(Step 4)

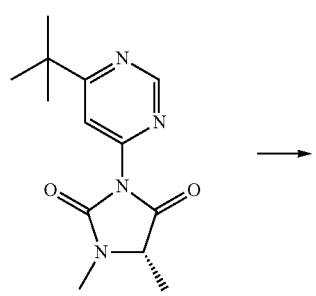

Approximately 10% of the minor enantiomers ((4R,5S)-1-(6-tert-butylpyrimidin-4-yl)-5-hydroxy-3,4-dimethyl-imidazolidin-2-one and (4R,5R)-1-(6-tert-butylpyrimidin-4-yl)-5-hydroxy-3,4-dimethyl-imidazolidin-2-one) was detected by chiral HPLC analysis. Levels of these enantiomeric products could be reduced by keeping the reaction temperature below −10° C. in similar reactions.

LC-MS: (positive ES MH+265).

Major diastereoisomer: 8.75 (s, 1H), 8.23 (s, 1H), 5.60 (d, 1H), 5.00 (very br s, 1H), 3.53 (m, 1H), 2.93 (s, 3H), 1.32-1.35 (m, 12H).

Minor diastereoisomer: 8.76 (s, 1H), 8.24 (s, 1H), 5.96 (d, 1H), 3.76 (m, 1H), 2.88 (s, 3H), 1.38 (d, 3H), 1.34 (s, 9H).

Table 1 lists examples of compounds of the general formula (I)

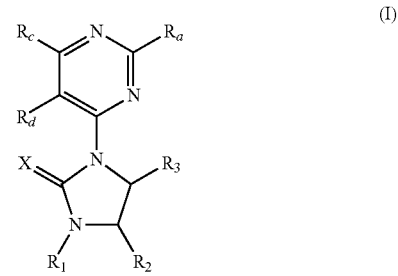

wherein $R^a$, $R^c$, $R^d$, $R^1$, $R^2$, $R^3$ and X are as defined above.

These compounds were made by the general methods described.

TABLE 1

| Example | STRUCTURE | 1H NMR (measured in CDCl₃ unless otherwise indicated) δ | LC-MS |
|---|---|---|---|
| A1 | 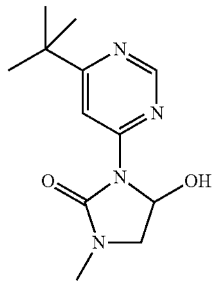 [SMILES: CN1CC(O)N(c2cc(C(C)(C)C)ncn2)C1=O] | 8.77 (s, 1H), 8.24 (s, 1H), 6.07 (m, 1H), 5.00 (br s, 1H), 3.71 (dd, 1H), 3.40 (dd, 1H), 2.95 (s, 3H), 1.36 (s, 9H). | positive ES MH+ 251 |
| A2 | 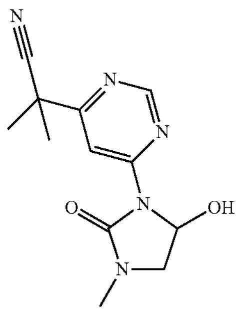 [SMILES: CN1CC(O)N(c2cc(C(C)(C)C#N)ncn2)C1=O] | 8.82 (s, 1H), 8.44 (s, 1H), 6.08 (m, 1H), 4.77 (br s, 1H), 3.73 (dd, 1H), 3.41 (dd, 1H), 2.96 (s, 3H), 1.74 (s, 6H). | positive ES MH+ 262 |
| A3 | 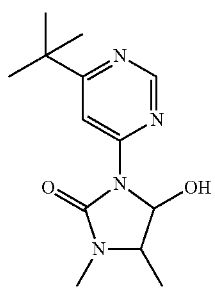 [SMILES: CC1C(O)N(c2cc(C(C)(C)C)ncn2)C(=O)N1C] | Major diastereoisomer: 8.75 (s, 1H), 8.23 (s, 1H), 5.60 (d, 1H), 5.00 (very br s, 1H), 3.53 (m, 1H), 2.93 (s, 3H), 1.32-1.35 (m, 12H).<br>Minor diastereoisomer: 8.76 (s, 1H), 8.24 (s, 1H), 5.96 (d, 1H), 3.76 (m, 1H), 2.88 (s, 3H), 1.38 (d, 3H), 1.34 (s, 9H). | positive ES MH+ 265 |
| A4 | 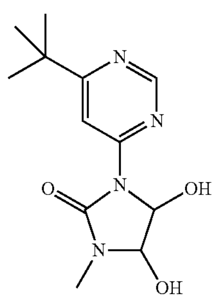 [SMILES: CN1C(=O)N(c2cc(C(C)(C)C)ncn2)C(O)C1O] | Major diastereoisomer: 8.69 (d, 1H), 8.14 (d, 1H), 5.71 (s, 1H), 4.98 (s, 1H), 2.99 (s, 3H), 1.34 (s, 9H).<br>Minor diastereoisomer: 8.75 (d, 1H); 8.21 (d, 1H); 5.92 (d, 1H); 5.13 (d, 1H); 2.96 (s, 3H); 1.34 (s, 9H). | positive ES MH+ 267 |
| A5 | 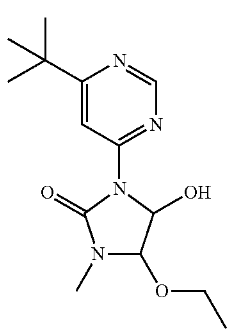 [SMILES: CCOC1C(O)N(c2cc(C(C)(C)C)ncn2)C(=O)N1C] | 8.76 (d, 1H), 8.16 (d, 1H), 5.72 (d, 1H), 4.80 (d, 1H), 4.70 (s, 1H), 3.65 (ddq, 2H), 2.99 (s, 3H), 1.34 (s, 9H), 1.27 (t, 3H). | positive ES MH+ 295 |

TABLE 1-continued

| Example | STRUCTURE | 1H NMR (measured in CDCl₃ unless otherwise indicated) δ | LC-MS |
|---------|-----------|------------------------------------------------------|-------|
| A6 | 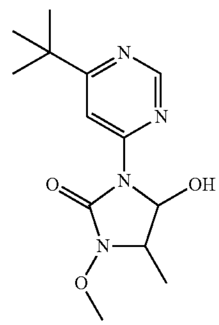 [SMILES: CON1C(=O)N(c2cc(C(C)(C)C)ncn2)C(O)C1C] | Major diastereoisomer: 8.79 (d, 1H), 8.24 (s, 1H), 5.53 (d, 1H), 5.10 (very br s, 1H), 3.90 (s, 3H), 3.70 (m, 1H), 1.44 (d, 3H), 1.35 (s, 9H). Minor diastereoisomer: 8.82 (d, 1H), 8.24 (s, 1H), 5.87 (d, 1H), 4.60 (very br s, 1H), 3.93 (s, 3H), 3.79 (m, 1H), 1.48 (d, 3H), 1.35 (s, 9H). | positive ES MH+ 281 |
| A7 | 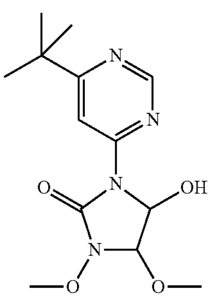 [SMILES: COC1C(O)N(c2cc(C(C)(C)C)ncn2)C(=O)N1OC] | 8.79 (s,1H), 8.15 (s, 1H), 5.68 (t, 1H), 4.95 (d, 1H), 4.86 (d, 1H), 3.96 (s, 3H), 3.61 (s, 3H), 1.35 (s, 9H). | positive ES MH+ 297 |
| A8 | 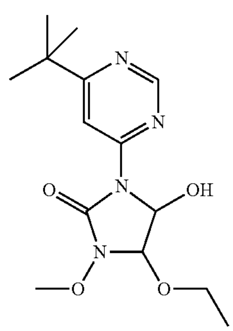 [SMILES: CCOC1C(O)N(c2cc(C(C)(C)C)ncn2)C(=O)N1OC] | 8.78 (s, 1H), 8.15 (s, 1H), 5.68 (t, 1H), 4.95 (d, 1H), 4.93 (d, 1H), 3.95 (s, 3H), 3.89 (m, 1H), 3.78 (m, 1H), 1.35 (s, 9H), 1.30 (t, 3H). | positive ES MH+ 311 |
| A9 | 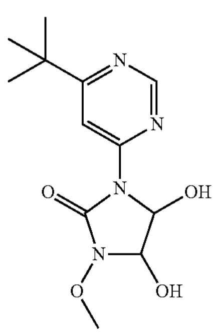 [SMILES: CON1C(=O)N(c2cc(C(C)(C)C)ncn2)C(O)C1O] | Major diastereoisomer: 8.80 (s, 1H), 8.17 (s, 1H), 5.74 (s, 1H), 5.28 (s, 1H), 4.90 (br s, 1H), 3.95 (s, 3H), 1.35 (s, 9H). Minor diastereoisomer: 8.83 (s, 1H), 8.22 (s, 1H), 5.88 (d, 1H), 5.22 (d, 1H), 4.95 (br s, 1H), 4.00 (s, 3H), 1.35 (s, 9H). | positive ES MH+ 283 |

TABLE 1-continued

| Example | STRUCTURE | 1H NMR (measured in CDCl₃ unless otherwise indicated) δ | LC-MS |
|---|---|---|---|
| A10 | 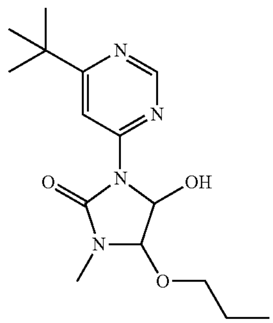 [SMILES: CCCOC1C(O)N(c2cc(C(C)(C)C)ncn2)C(=O)N1C] | 8.76 (d, 1H), 8.17 (d, 1H), 5.72 (d, 1H), 4.79 (d, 1H), 4.70 (s, 1H), 3.54 (m, 2H), 2.99 (s, 3H), 1.65 (m, 2H), 1.34 (s, 9H), 0.96 (t, 3H). | positive ES MH+ 309 |
| A11 | 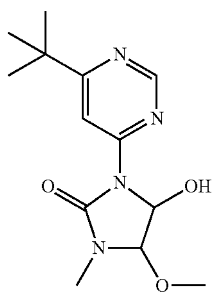 [SMILES: COC1C(O)N(c2cc(C(C)(C)C)ncn2)C(=O)N1C] | 8.76 (d, 1H), 8.25 (d, 1H), 5.75 (s, 1H), 4.88 (br.s, 1H), 4.66 (s, 1H), 3.42 (s, 3H); 3.00 (s, 3H), 1.35 (s, 9H). | positive ES MH+ 281 |
| A12 and A13: (isomers 1 and 3) | | As for example A3 | As for example A3 |
| A14 and A15: (isomers 2 and 4) | | As for example A3 | As for example A3 |
| A16 | 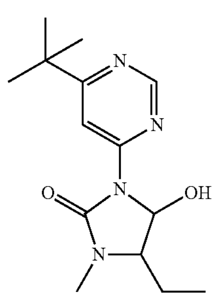 [SMILES: CCC1C(O)N(c2cc(C(C)(C)C)ncn2)C(=O)N1C] | 8.75 (s, 1H), 8.23 (s, 1H), 5.60 (d, 1H), 4.96 br s, 1H), 3.40 (m, 1H), 2.90 (s, 3H), 1.80 (m, 1H), 1.55 (m, 1H), 1.35 (s, 9H), 0.95 (t, 3H). | positive ES MH+ 279 |

TABLE 1-continued

| Example | STRUCTURE | 1H NMR (measured in CDCl₃ unless otherwise indicated) δ | LC-MS |
|---|---|---|---|
| A17 | 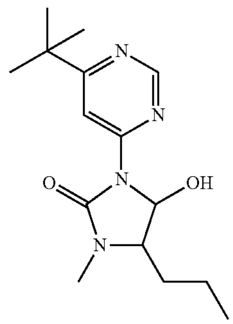 [SMILES: CCCC1C(O)N(c2cc(C(C)(C)C)ncn2)C(=O)N1C] | 8.75 (s, 1H), 8.23 (s, 1H), 5.70 (d, 1H), 4.90 br s, 1H), 3.40 (m, 1H), 2.90 (s, 3H), 1.35-1.80 (m, 4H), 1.35 (s, 9H), 0.95 (t, 3H). | positive ES MH+ 293 |
| A18 | 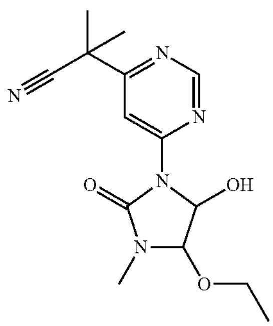 [SMILES: CCOC1C(O)N(c2cc(C(C)(C)C#N)ncn2)C(=O)N1C] | 8.82 (d, 1H), 8.38 (d, 1H), 5.72 (s, 1H), 4.70 (s, 1H), 3.65 (m, 2H), 2.99, (s, 3H), 1.74 (s, 6H), 1.27 (t, 3H). | positive ES MH+ 306 |
| A19 | 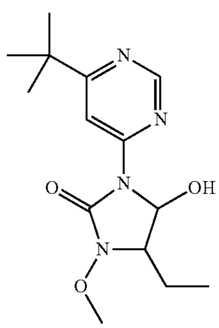 [SMILES: CCC1C(O)N(c2cc(C(C)(C)C)ncn2)C(=O)N1OC] | Major diastereoisomer: 8.55 (s, 1H), 8.43 (dd, 1H), 7.25 (d, 1H), 5.55 (d, 1H), 5.04 (very br s, 1H), 3.90 (s, 3H), 3.38 (d, 1H), 1.95 (m, 2H), 1.35 (s, 9H), 1.05 (m, 3H). Minor diastereoisomer: 8.53 (s, 1H), 8.45 (dd, 1H), 7.24 (d, 1H), 5.87 (d, 1H), 4.60 (very br s, 1H), 3.93 (s, 3H), 3.71 (m, 1H), 1.70 (m, 2H), 1.35 (s, 9H), 1.05 (m, 3H). | positive ES MH+ 295 |
| A20 | 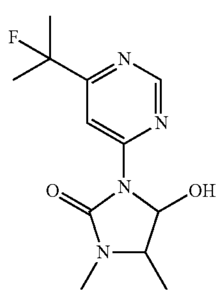 [SMILES: CC1C(O)N(c2cc(C(C)(C)F)ncn2)C(=O)N1C] | Major diastereoisomer: 8.74 (s, 1H), 8.39 (s, 1H), 5.60 (m, 1H), 4.87 (m, 1H), 3.56-3.51 (m, 1H), 2.93 (s, 3H), 1.65 (d, 6H), 1.34 (d, 3H) Minor diastereoisomer: 8.74 (s, 1H), 8.39 (s, 1H), 5.99-5.94 (m, 1H), 4.71 (m, 1H), 3.81-3.75 (m, 1H), 2.89 (s, 3H), 1.71 (d, 6H), 1.39 (d, 3H) | positive ES MH+ 269 |
| A21 | 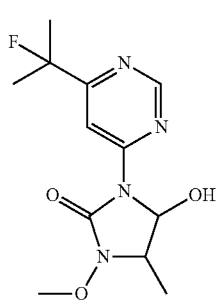 [SMILES: CON1C(=O)N(c2cc(C(C)(C)F)ncn2)C(O)C1C] | Major diastereoisomer: 8.79 (s, 1H), 8.39 (s, 1H), 5.54 (d, 1H), 4.99 (m, 1H), 3.90 (s, 3H), 3.77-3.67 (m, 1H), 1.68-1.65 (m, 6H), 1.45 (d, 3H) Minor diastereoisomer: 8.81 (s, 1H), 8.39 (s, 1H), 5.88 (d, 1H), 4.51 (m, 1H), 3.92 (s, 3H), 3.85-3.78 (m, 1H), 1.73-1.70 (m, 6H), 1.49 (d, 3H) | positive ES MH+ 285 |

TABLE 1-continued

| Example | STRUCTURE | 1H NMR (measured in CDCl₃ unless otherwise indicated) δ | LC-MS |
|---|---|---|---|
| A22 | 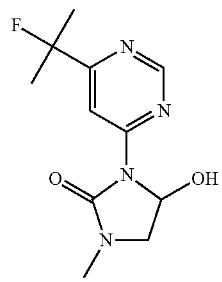 [SMILES: CN1CC(O)N(c2cc(C(C)(C)F)ncn2)C1=O] | 8.75 (s, 1H), 8.39 (s, 1H), 6.06 (m, 1H), 4.90 (m, 1H), 3.75-3.68 (dd, 1H), 3.42-3.37 (dd, 1H), 2.96 (s, 3H), 1.70 (d, 3H), 1.65 (d, 3H) | positive ES MH+ 255 |
| A23 | 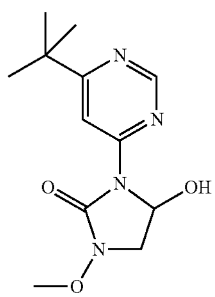 [SMILES: CON1CC(O)N(c2cc(C(C)(C)C)ncn2)C1=O] | 8.75 (s, 1H), 8.13 (s, 1H), 5.95 (br d, 1H), 4.90 (very br s, 1H), 3.80 (s, 3H), 3.70 (m, 1H), 3.05 (m, 1H), 1.25 (s, 9H) | positive ES MH+ 267 |
| A24 | 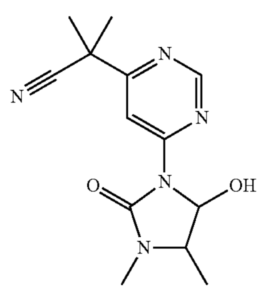 [SMILES: CC1C(O)N(c2cc(C(C)(C)C#N)ncn2)C(=O)N1C] | Major diastereoisomer: 8.80 (s, 1H), 8.44 (s, 1H), 5.60 (t, 1H), 4.75 (d, 1H), 3.54 (m, 1H), 2.93 (s, 3H), 1.75 (s, 6H), 1.35 (d, 3H) Minor diastereoisomer: 8.81 (s, 1H), 8.44 (d, 1H), 5.97 (dd, 1H), 4.59 (d, 1H), 3.79 (m, 1H), 2.89 (s, 3H), 1.75 (s, 6H), 1.38 (d, 3H) | positive ES MH+ 276 |
| A25 | 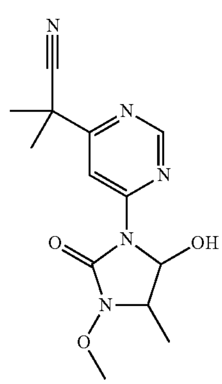 [SMILES: CON1C(=O)N(c2cc(C(C)(C)C#N)ncn2)C(O)C1C] | Major diastereoisomer: 8.84 (d, 1H), 8.42 (d, 1H), 5.54 (dd, 1H), 4.86 (d, 1H), 3.82 (s, 3H), 3.73 (m, 1H), 1.77 (s, 6H), 1.30 (m, 3H) Minor diastereoisomer: 8.87 (d, 1H), 8.42 (d, 1H), 5.90 (dd, 1H), 4.41 (d, 1H), 3.89 (s, 3H), 3.80 (m, 1H), 1.77 (s, 6H), 1.46 (m, 3H) | positive ES MH+ 292 |

TABLE 1-continued
| Example | STRUCTURE | 1H NMR (measured in CDCl₃ unless otherwise indicated) δ | LC-MS |
|---------|-----------|---------------------------------------------------------|-------|
| A26 | 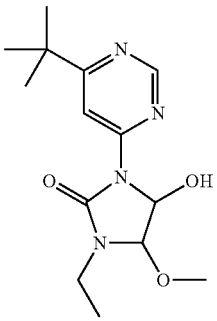 [SMILES: CCN1C(=O)N(c2cc(C(C)(C)C)ncn2)C(O)C1OC] | 8.77 (d, 1H), 8.16 (d, 1H), 5.75 (d, 1H), 4.80 (d, 1H), 4.74 (s, 1H), 3.56 (m, 1H), 3.41 (s, 3H), 3.33 (m, 1H), 1.35 (s, 9H), 1.25 (t, 3H) | positive ES MH+ 295 |
| A27 | 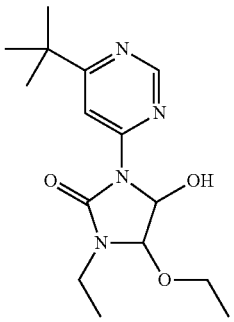 [SMILES: CCOC1C(O)N(c2cc(C(C)(C)C)ncn2)C(=O)N1CC] | 8.76 (d, 1H), 8.16 (d, 1H), 5.73 (d, 1H), 4.79 (d, 1H), 4.78 (s, 1H), 3.51-3.72 (m, 3H), 3.33 (m, 1H), 1.34 (s, 9H), 1.27 (t, 3H), 1.25 (t, 3H) | positive ES MH+ 309 |
| A28 | 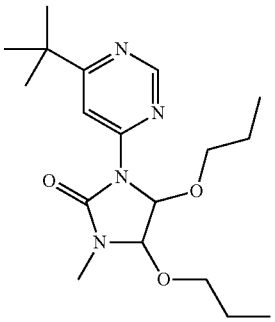 [SMILES: CCCOC1C(OCCC)N(c2cc(C(C)(C)C)ncn2)C(=O)N1C] | 8.81 (s, 1H), 8.30 (s, 1H), 5.74 (s, 1H), 4.66 (s, 1H), 3.71 (m, 2H), 3.46 (m, 2H), 2.98 (s, 3H), 1.62 (m, 4H), 1.35 (s, 9H), 0.92 (m, 6H) | positive ES MH+ 351 |
| A29 | 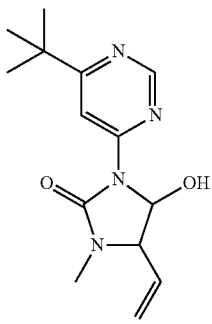 [SMILES: C=CC1C(O)N(c2cc(C(C)(C)C)ncn2)C(=O)N1C] | Major diastereoisomer: 8.75 (s, 1H), 8.24 (s, 1H), 5.74 (ddd, 1H), 5.70 (m, 1H), 5.44 (m, 1H), 5.43 (m, 1H), 4.97 (br s, 1H), 3.88 (m, 1H), 2.88 (s, 3H), 1.36 (s, 9H). Minor diastereoisomer: 8.77 (s, 1H), 8.25 (s, 1H), 6.03 (m, 1H), 5.96 (m, 1H), 5.52 (m, 1H), 5.47 (m, 1H), 4.86 (br s, 1H), 4.07 (m, 1H), 2.83 (s, 3H), 1.36 (s, 9H). | positive ES MH+ 277 |

TABLE 1-continued
| Example | STRUCTURE | 1H NMR (measured in CDCl₃ unless otherwise indicated) δ | LC-MS |
|---|---|---|---|
| A30 | 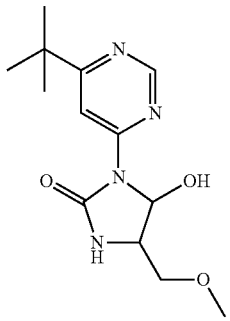 [SMILES: COCC1NC(=O)N(c2cc(C(C)(C)C)ncn2)C1O] | 8.78 (s, 1H), 8.21 (s, 1H), 5.81 (t, 1H), 5.33 (br s, 1H), 4.99 (d, 1H), 3.8 (m, 1H), 3.54 (m, 1H), 3.41 (s, 3H), 1.35 (s, 9H). | positive ES MH+ 281 |
| A31 | 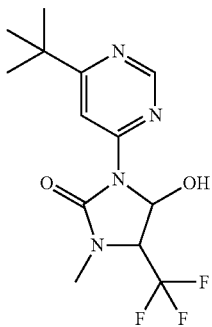 [SMILES: CN1C(=O)N(c2cc(C(C)(C)C)ncn2)C(O)C1C(F)(F)F] | 8.78 (s, 1H), 8.15 (s, 1H), 6.04 (s, 1H), 5.11 (br s, 1H), 3.93 (dq, 1H), 3.10 (s, 3H), 1.36 (s, 9H). | positive ES MH+ 319 |
| A32 | 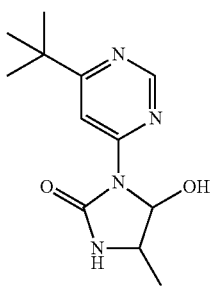 [SMILES: CC1NC(=O)N(c2cc(C(C)(C)C)ncn2)C1O] |  | positive ES MH+ 251 |
| A33 | 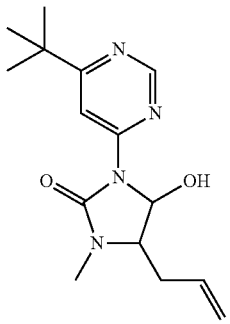 [SMILES: C=CCC1C(O)N(c2cc(C(C)(C)C)ncn2)C(=O)N1C] | Major diastereomer 8.75 (d, 1H), 8.22 (d, 1H), 5.75 (m, 1H), 5.71 (d, 1H); 5.24 (dd, 1H), 5.20 (dd, 1H), 4.94 (br.s, 1H), 3.54 (ddd, 1H), 2.95 (s, 3H), 2.54 (m, 1H), 2.35 (m, 1H), 1.34 (s, 9H). Minor diastereomer 8.76 (d, 1H), 8.23 (d, 1H), 5.99 (m, 1H), 5.71 (d, 1H), 5.24 (dd, 1H), 5.20 (dd, 1H), 4.85 (br.s, 1H), 3.65 (m, 1H), 2.90 (s, 3H), 2.65 (m, 1H), 2.35 (m, 1H), 1.34 (s, 9H). | positive ES MH+ 291 |

TABLE 1-continued

| Example | STRUCTURE | 1H NMR (measured in CDCl$_3$ unless otherwise indicated) δ | LC-MS |
|---|---|---|---|
| A34 | 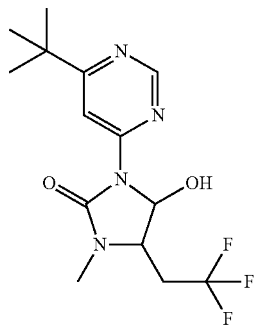 [SMILES: CN1C(=O)N(c2cc(C(C)(C)C)ncn2)C(O)C1CC(F)(F)F] | 8.78 (d, 1H), 8.16 (d, 1H), 5.88 (t, 1H), 4.86 (d, 1H), 3.74 (m, 1H), 2.97 (s, 3H), 2.42 (m, 2H), 1.35 (s, 9H). | positive ES MH+ 333 |
| A35 | 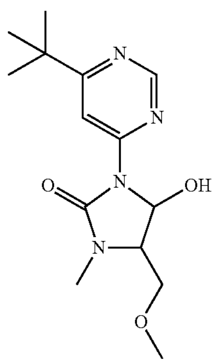 [SMILES: COCC1C(O)N(c2cc(C(C)(C)C)ncn2)C(=O)N1C] | 8.79 (s, 1H), 8.25 (s, 1H), 5.82 (s, 1H), 4.98 (d, 1H), 3.58 (br s, 3H), 3.39 (s, 3H), 2.97 (s, 3H), 1.36 (s, 9H). | positive ES MH+ 295 |
| A36 | 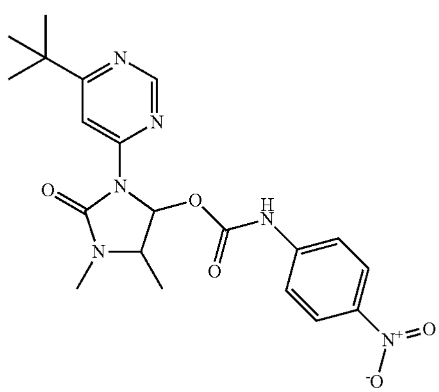 | 8.78 (s, 1H), 8.35 (br s, 1H), 8.29 (s, 1H), 8.20 (d, 2H), 7.61 (d, 2H), 6.67 (s, 1H), 3.72 (q, 1H), 2.95 (s, 3H), 1.40 (d, 3H), 1.32 (s, 9H). | positive ES MH+ 429 |
| A37 | 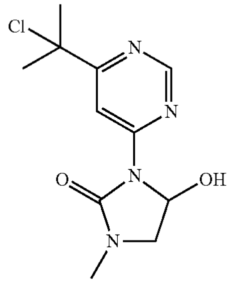 | 8.80 (br s, 1H), 8.56 (br s, 1H), 6.03-6.16 (m, 1H), 4.84 (br s, 1H), 3.70-3.75 (m, 1H), 3.39-3.47 (m, 1H), 2.97 (s, 3H), 1.97 (br s, 6H). | positive ES MH+ 292 |

TABLE 1-continued

| Example | STRUCTURE | 1H NMR (measured in CDCl₃ unless otherwise indicated) δ | LC-MS |
|---|---|---|---|
| A38 | 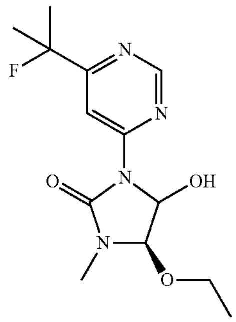 [SMILES: CCO[C@@H]1C(O)N(c2cc(C(C)(C)F)ncn2)C(=O)N1C] | As for example A42 | As for example A42 |
| A39 | 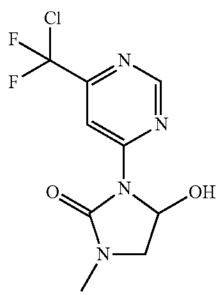 [SMILES: CN1CC(O)N(c2cc(C(F)(F)Cl)ncn2)C1=O] | 8.92 (s, 1H), 8.58 (d, 1H), 6.11 (dd, 1H), 4.65 (br. s., 1H), 3.76 (dd, 1H), 3.43 (dd, 1H), 2.98 (s, 3H). | positive ES MH+ 279 |
| A40 | 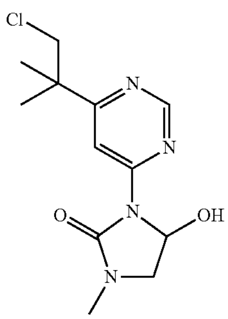 [SMILES: CN1CC(O)N(c2cc(C(C)(C)CCl)ncn2)C1=O] | 8.66-8.87 (m, 1H), 8.13-8.34 (m, 1H), 5.96-6.18 (m, 1H), 4.61-5.04 (bs, 1H), 3.77-3.92 (m, 2H), 3.62-3.75 (m, 1H), 3.40 (dd, J = 10.4, 2.6 Hz, 1H), 2.96 (s, 3H), 1.43 ppm (d, 6H). | positive ES MH+ 285 |
| A41 | 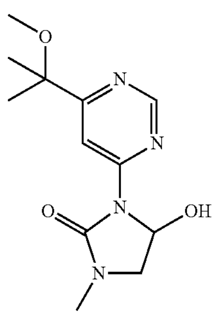 [SMILES: COC(C)(C)c1cc(N2C(=O)N(C)CC2O)ncn1] | 8.8 (s, 1H), 8.38 (s, 1H), 6.08 (m, 1H), 4.93 (br s, 1H), 3.72 (m, 1H), 3.41 (m, 1H), 3.24 (s, 3H), 2.97 (s, 3H), 1.55 (s, 3H), 1.53 (s, 3H) | positive ES MH+ 267 |
| A42 | 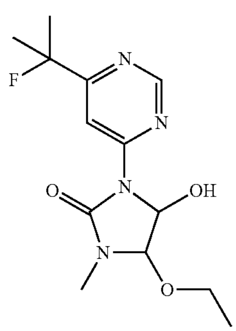 [SMILES: CCOC1C(O)N(c2cc(C(C)(C)F)ncn2)C(=O)N1C] | 8.76 (s, 1H), 8.34 (t, 1H), 5.74 (d, 1H), 4.72 (s, 1H), 4.69 (d, 1H), 3.75-3.57 (m, 2H), 3.00 (s, 3H), 1.71 (d, 3H), 1.66 (d, 3H), 1.29 (t, 3H). | positive ES MH+ 299 |

TABLE 1-continued

| Example | STRUCTURE | 1H NMR (measured in CDCl₃ unless otherwise indicated) δ | LC-MS |
|---------|-----------|---------------------------------------------------------|-------|
| A43 | 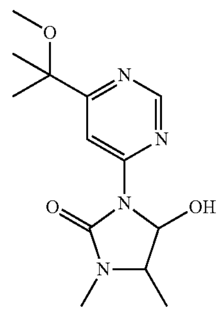 [SMILES: COC(C)(C)c1cc(N2C(=O)N(C)C(C)C2O)ncn1] | Major diastereoisomer: 8.78 (s, 1H), 8.36 (s, 1H), 5.61 (s, 1H), 3.53 (m, 1H), 3.23 (s, 3H), 2.92 (s, 3H), 1.54 (s, 3H), 1.52 (s, 3H), 1.34 (d, 3H)<br>Minor diastereoisomer: 8.79 (s, 1H), 8.37 (s, 1H), 5.97 (d, 1H), 3.78 (m, 1H), 3.23 (s, 3H), 2.89 (s, 3H), 1.54 (s, 3H), 1.52 (s, 3H), 1.38 (d, 3H) | positive ES MH+ 281 |
| A44 | 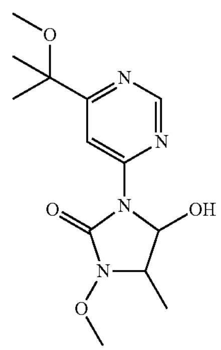 [SMILES: CON1C(=O)N(c2cc(C(C)(C)OC)ncn2)C(O)C1C] | Major diastereoisomer: 8.88 (s, 1H), 8.43 (s, 1H), 5.57 (d, 1H), 3.91 (s, 3H), 3.75 (m, 1H), 3.27 (s, 3H), 1.58 (s, 3H), 1.57 (s, 3H), 1.46 (d, 3H).<br>Minor diastereoisomer: 8.92 (s, 1H), 8.44 (s, 1H), 5.92 (d, 1H), 3.93 (s, 3H), 3.83 (m, 1H), 3.27 (s, 3H), 1.57 (s, 3H), 1.56 (s, 3H), 1.5 (d, 3H). | positive ES MH+ 297 |
| A45 | 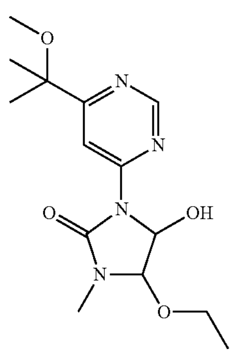 [SMILES: CCOC1C(O)N(c2cc(C(C)(C)OC)ncn2)C(=O)N1C] | 8.91 (s, 1H), 8.41 (s, 1H), 5.79 (s, 1H), 4.73 (s, 1H), 3.69 (m, 2H), 3.27 (s, 3H), 3.01 (s, 3H), 1.58 (s, 3H), 1.57 (s, 3H), 1.29 (t, 3H) | positive ES MH+ 311 |
| A46 | 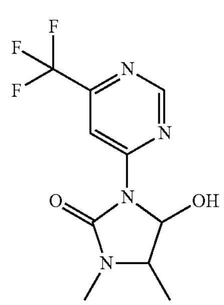 [SMILES: CC1C(O)N(c2cc(C(F)(F)F)ncn2)C(=O)N1C] | Major diastereoisomer: 8.92 (s, 1H), 8.61 (s, 1H), 5.64 (t, 1H), 4.65 (m, 1H), 3.57 (dq, 1H), 2.94 (s, 3H), 1.36 (d, 3H).<br>Minor diastereoisomer: 8.93 (s, 1H), 8.62 (s, 1H), 6.01 (dd, 1H), 4.48 (m, 1H), 3.83 (pentet, 1H), 2.91 (s, 3H), 1.40 (d, 3H). | positive ES MH+ 277 |

TABLE 1-continued

| Example | STRUCTURE | 1H NMR (measured in CDCl₃ unless otherwise indicated) δ | LC-MS |
|---|---|---|---|
| A47 | 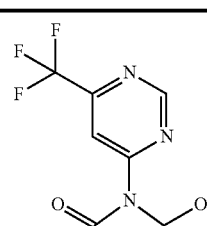 | | positive ES MH+ 263 |

Example 7

Preparation of 2-(6-chloropyrimidin-4-yl)-2-methyl-propanenitrile as Used for Synthesis of Examples of the Type A2, A24 and A25

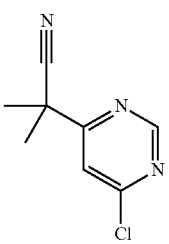

Procedure for synthesis of 2-(6-chloropyrimidin-4-yl)-2-methyl-propanenitrile (Step-1): Synthesis of tert-butyl 2-(6-chloropyrimidin-4-yl)-2-cyano-acetate 4,6-dichloropyrimidine (commercially available) (150 g, 1006.847 mmol) and tert-butyl-2-cyanoacetate (2.5 equiv., 2517.116 mmol) were dissolved in THF (10 mL/g). This was then cooled to 0° C. and sodium hydride (2.5 equiv, 2517.1 mmol) was added portion wise over 30 min. Then reaction mixture was stirred at rt for 2 h. then quenched with sat NH₄Cl and extracted with ethyl acetate. Combined organic layers were dried over sodium sulphate, filtered and concentrated under reduced pressure. Crude product was purified by column chromatography to give desired tert-butyl 2-(6-chloropyrimidin-4-yl)-2-cyano-acetate.

Procedure for Synthesis of 2-(6-chloropyrimidin-4-yl)-2-methyl-propanenitrile (Steps 2 and 3): Synthesis of tert-butyl 2-(6-chloropyrimidin-4-yl)-2-cyano-acetate

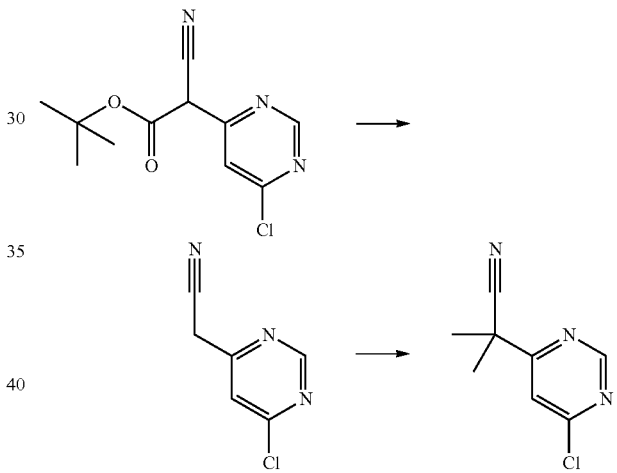

Step 2:

Tert-butyl-2-(6-chloropyrimidin-4-yl)-2-cyano-acetate (150 g, 591.3 mmol) was suspended in dichloromethane (10 mL/g) and trifluoroacetic acid (15 equiv., 11232.5 mmol) was added at room temp. The reaction mixture was stirred at rt for 2 h. then water was added and DCM layer was separated. The water layer was again extracted with DCM (500 mL×3). Combined organic layers were dried over sodium sulphate, filtered and concentrated under reduced pressure. This crude 2-(6-chloropyrimidin-4-yl)acetonitrile material was used for the next step with out further purification.

Step 3:

2-(6-chloropyrimidin-4-yl)acetonitrile (150 g, 976.7406 mmol) was dissolved in DMF (10 mL/g, 19400 mmol) and treated with methyl iodide (5 equiv., 4883.7 mmol) and K₂CO₃ (5 equiv., 4883.7 mmol) at room temperature. then the reaction mixture was stirred at rt overnight. Water was then added and the reaction was extracted with ethyl acetate. The combined organic layers were dried over sodium sulphate, filtered and concentrated under reduced pressure. The crude product was purified by column chromatography to give 2-(6-chloropyrimidin-4-yl)-2-methyl-propanenitrile. LC-MS: positive ES MH+182

Example 8

Preparation of 4-chloro-6-(1-fluoro-1-methyl-ethyl)pyrimidine as Used for Synthesis of Examples of the Type A20, A21 and A22

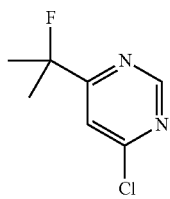

Procedure for Synthesis of 4-chloro-6-(1-fluoro-1-methyl-ethyl)pyrimidine (Step-1)

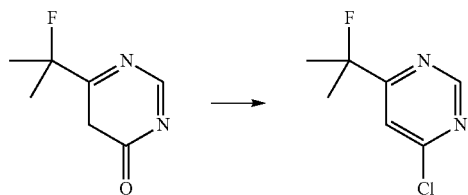

4-(1-fluoro-1-methyl-ethyl)-1H-pyrimidin-6-one (synthesis as described in WO9944997) (5.573 g, 35.69 mmol, 5.573 g) was suspended in POCl$_3$ (55.27 g, 356.9 mmol, 10 equiv., 33.60 mL) and the reaction mixture was heated to 80° C. for 2 hours. The reaction mixture was allowed to cool to ambient temperature, where left to stand overnight without stirring. The reaction mixture was concentrated in vacuo to remove the excess POCl$_3$. The resulting residue was quenched carefully with water to destroy any remaining POCl$_3$. The aqueous was extracted with DCM (×2). The organics were combined and concentrated in vacuo to yield crude product as an orange oil, which was purified by silica chromatography to give desired product as as a colourless oil (4.269 g).
LC-MS: positive ES MH+175

Example 9

Preparation of 1,1,3-trimethoxy-N-methyl-propan-2-amine as Used for Synthesis of Examples of the Type A30 and A35

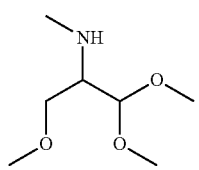

Procedure for Synthesis of 1,1,3-trimethoxy-N-methyl-propan-2-amine (Step 1)

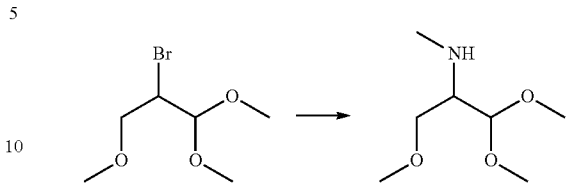

A solution of 2-bromo-1,1,3-trimethoxy-propane (commercially available) (7 g, 32.85 mmol) in methylamine (40% aqueous solution) (105 mL, 210 mmol) was divided into seven equal portions and these were heated at 130° C. for 1 h in a microwave. The combined reaction mixtures were then concentrated and the residue obtained was treated with toluene and evaporated again. The residue was then stirred with DCM, filtered and evaporated to give the crude product that was taken to next step without further purification.

Example 10

Preparation of 1,1,1-trifluoro-3,3-dimethoxy-N-methyl-propan-2-amine as Used for Synthesis of Examples of the Type A31

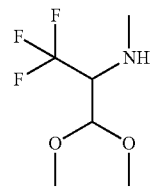

Procedure for Synthesis of 2,2-dimethoxy-N-methyl-ethanimine (Step 1)

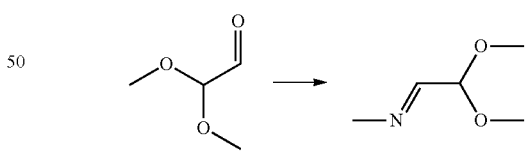

Methylamine hydrochloride (4.05 g, 1.05 equiv.) in DCM (60 mL) was cooled to 0° C., then K$_2$CO$_3$ (5.53 g, 1 equiv.) was added over 5 minutes. Reaction was stirred at 0° C. for a further 10 minutes then 2,2-dimethoxyacetaldehyde (6.04 mL, 40 mmol) was added and the reaction was stirred vigorously at 0° C. After 5 minutes at 0° C., the reaction was allowed to warm to room temperature. After 15 minutes at room temperature, DCM was decanted off, solid was extracted with DCM (2×15 mL). Combined DCM fractions were dried (Na$_2$SO$_4$), filtered, and evaporated to give product which was used without further purification (4.10 g, 87%).

Procedure for Synthesis of 1,1,1-trifluoro-3,3-dimethoxy-N-methyl-propan-2-amine (Step 2)

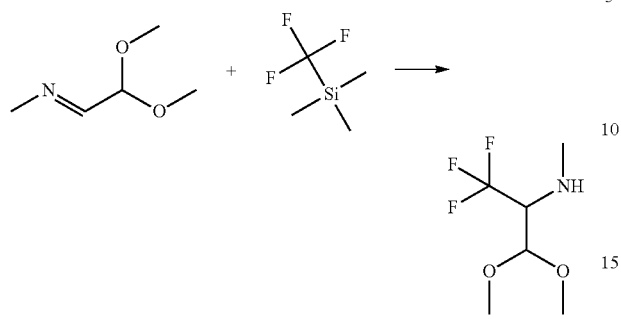

KHF$_2$ (2.01 g, 0.75 equiv.) was suspended in MeCN (69 mL) and DMF (8.0 mL) under Nitrogen, and cooled to 0° C. then 2,2-dimethoxy-N-methyl-ethanimine (4.02 g, 1 equiv.) was added followed by dropwise addition of TFA (3.28 mL, 1.25 equiv.) over 2 minutes. Reaction was stirred at 0° C. for 5 minutes, then trimethyl(trifluoromethyl)silane (7.6 mL, 1.5 equiv.) was added over 5 minutes and the reaction was stirred at 0° C. for 3 h. Reaction was then treated with sat. aqueous NaHCO3 (50 mL) over 3 minutes The reaction mixture was then extracted with diethyl ether (3×200 mL), dried (Na$_2$SO$_4$), filtered and evaporated (care as product is volatile) to give product (14.1 g, 44%), which was used without further purification.

Example 11

Preparation of 4-chloro-6-(1-chloro-1-methyl-ethyl)pyrimidine as Used for Synthesis of Examples of the Type A37

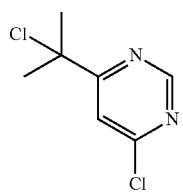

Procedure for Synthesis of 1,1,1-trifluoro-3,3-dimethoxy-N-methyl-propan-2-amine (Step 1)

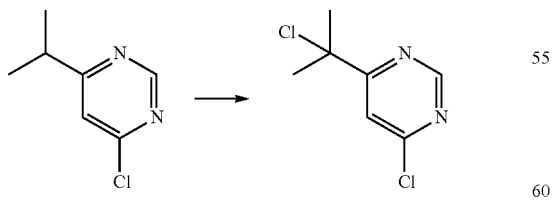

4-chloro-6-isopropyl-pyrimidine (commercially available, 0.2 g, 1.277 mmol) was dissolved in carbon tetrachloride (0.2 mL) and then N-chlorosuccinimide (0.197 g, 1.40 mmol) and benzoyl benzenecarboperoxoate (0.0639 mmol, 0.015 g) were added. The reaction mixture was heated in a microwave at 150° C. for 60 mins. The reaction mixture was then was purified directly by silica chromatography to give desired product (40 mg, 16%), which was used in the next reaction without further purification.

Example 12

Preparation of 4-chloro-6-[chloro(difluoro)methyl]pyrimidine as Used for Synthesis of Examples of the Type A39

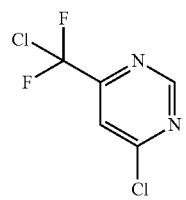 [SMILES: FC(F)(Cl)c1cc(Cl)ncn1]

Procedure for Synthesis of 4-chloro-6-[chloro(difluoro)methyl]pyrimidine (Step 1)

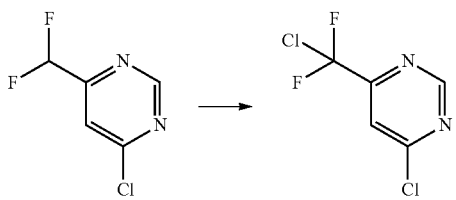 [SMILES: FC(F)c1cc(Cl)ncn1 ; FC(F)(Cl)c1cc(Cl)ncn1]

4-chloro-6-(difluoromethyl)pyrimidine (commercially available) (820 mg, 4.98 mmol) was dissolved in CCl$_4$ (5 ml). Nitrogen gas was bubbled through for 5 mins, then reaction mixture was cooled to 5° C. then tBuOCl (1.3 eq, 0.74 ml, freshly made) was added and stirred at 5° C. and reaction irradiated with 254 nm UV probe for 7.25 h. Reaction mixture was evaporated, diluted with isohexane (2 mL), then chromatographed on silica (eluting with 0-5% EtOAc in isohexane) to give desired product as a colourless oil (160 mg), which was used without further purification.
$^1$H NMR (CDCl$_3$): 9.15 (s, 1H), 7.68 (d, 1H).

Example 13

Preparation of 4-chloro-6-(2-chloro-1,1-dimethyl-ethyl)pyrimidine as Used for Synthesis of Examples of the Type A40

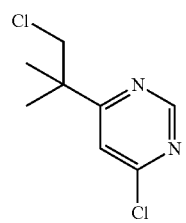

Procedure for Synthesis of 4-chloro-6-(2-chloro-1,1-dimethyl-ethyl)pyrimidine (Step 1)

Procedure for Synthesis of 4-chloro-6-(1-methoxy-1-methyl-ethyl)pyrimidine (Step 1)

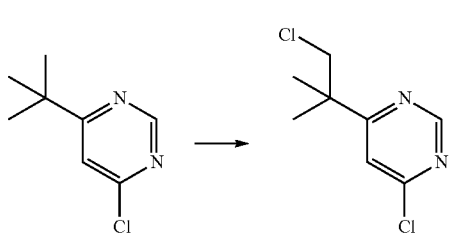

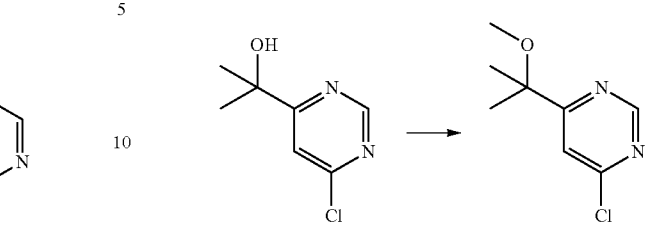

4-tert-butyl-6-chloro-pyrimidine (1 g, 5.86 mmol) was dissolved in carbon tetrachloride 29.30 mL) and N-chlorosuccinimide (0.90 g, 6.44 mmol) and benzoyl benzenecarboperoxoate (0.293 mmol, 0.071 g, 0.05) was added and the reaction mixture was heated in the microwave at 150° C. for 30 mins. The solvent was reduced in vacuo and purified by column chromatography (eluting with Hexane and Ethyl acetate) on a 15 µm silica column (for best separation of product). Fractions containing product were evaporated and giving 4-chloro-6-(2-chloro-1,1-dimethyl-ethyl)pyrimidine (655 mg, 54%).

$^1$H NMR (CDCl$_3$): 8.82-9.07 (m, 1H), 7.29-7.47 (m, 1H), 3.70-3.91 (m, 2H), 1.34-1.51 (m, 6H)

Example 14

Preparation of 4-chloro-6-(1-methoxy-1-methyl-ethyl)pyrimidine as Used for Synthesis of Examples of the Type A41

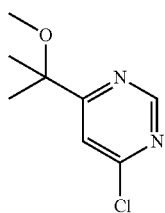

2-(6-chloropyrimidin-4-yl)propan-2-ol (for a synthesis see Dinnell, Kevin et al, WO2011045353) (130 mg, 0.75 mmol) dissolved in THF (2.6 mL) and then methyl iodide (1.51 mmol, 0.22 g). NaH (1.5 equiv., 60 mass %) was then added and the reaction was stirred at rt for 16 h.

The reaction mixture was then poured into water (500 mL), and then extracted with ethyl acetate (3×400 mL). The combined organic layers were dried over sodium sulfate and purified by silica column chromatography to give product as a colourless liquid (2.31 g, 15%), which was used without further purification.

Example 15

Herbicidal Action

Example 15a

Pre-Emergence Herbicidal Activity

Seeds of a variety of test species were sown in standard soil in pots. After cultivation for one day (pre-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table 2.

TABLE 2

| | | Application pre-emergence | | | | | |
|---|---|---|---|---|---|---|---|
| Example number | Rate (g/Ha) | ABUTH | AMARE | SETFA | ECHCG | ALOMY | ZEAMX |
| A1 | 1000 | 5 | 5 | 5 | 5 | 4 | 4 |
| A2 | 1000 | 4 | 5 | 5 | 4 | 4 | 3 |
| A3 | 1000 | 5 | 5 | 5 | 4 | 4 | 2 |
| A4 | 1000 | 4 | 5 | 2 | 2 | 2 | 0 |
| A5 | 1000 | 5 | 5 | 5 | 5 | 4 | 2 |
| A6 | 1000 | | 5 | 5 | 5 | 4 | |
| A7 | 1000 | 5 | 5 | 4 | 4 | 4 | 4 |
| A8 | 1000 | 5 | 5 | 5 | 5 | 5 | 1 |
| A9 | 1000 | 0 | 5 | 1 | 2 | 3 | 1 |
| A10 | 1000 | 4 | 5 | 4 | 2 | 4 | 2 |
| A11 | 1000 | 4 | 5 | 4 | 3 | 3 | 1 |
| A16 | 1000 | 5 | 5 | 5 | 4 | 2 | 2 |
| A17 | 1000 | 4 | 5 | 5 | 5 | 4 | 3 |
| A18 | 1000 | 5 | 5 | 4 | 3 | 1 | 2 |
| A19 | 1000 | 3 | 5 | 5 | 5 | 4 | 3 |

TABLE 2-continued

Application pre-emergence

| Example number | Rate (g/Ha) | ABUTH | AMARE | SETFA | ECHCG | ALOMY | ZEAMX |
|---|---|---|---|---|---|---|---|
| A20 | 1000 | 5 | 5 | 5 | 4 | 3 | 4 |
| A21 | 1000 | 5 | 5 | 5 | 4 | 3 | 3 |
| A22 | 1000 | 5 | 5 | 5 | 5 | 4 | 4 |
| A23 | 1000 | 5 | 5 | 2 | 4 | 1 | 1 |
| A24 | 1000 | 5 | 5 | 5 | 5 | 4 | 2 |
| A25 | 1000 | 5 | 5 | 5 | 5 | 4 | 4 |
| A26 | 1000 | 2 | 1 | 0 | 0 | 0 | 1 |
| A27 | 1000 | 1 | 1 | 0 | 0 | 0 | 0 |
| A28 | 1000 | 0 | 0 | 0 | 0 | 0 | 0 |
| A12 | 1000 | 5 | 5 | 5 | 5 |  | 3 |
| A13 | 1000 | 5 | 5 | 5 | 5 |  | 3 |
| A29 | 1000 | 5 | 5 | 4 | 4 | 4 | 1 |
| A30 | 1000 | 5 | 5 | 4 | 4 | 4 | 1 |
| A31 | 1000 | 2 | 2 | 4 | 3 | 3 | 0 |
| A32 | 1000 | 3 | 2 | 1 | 1 | 1 | 0 |
| A33 | 1000 | 5 | 5 | 4 | 5 | 4 | 3 |
| A34 | 1000 | 4 | 5 | 2 | 1 | 1 | 0 |
| A36 | 1000 | 5 | 5 | 4 | 4 | 4 | 3 |
| A37 | 1000 | 5 | 5 | 5 | 5 |  | 3 |
| A38 | 1000 | 5 | 5 | 5 | 5 |  | 2 |
| A39 | 1000 | 5 | 5 | 5 | 5 |  | 2 |
| A40 | 1000 | 5 | 5 | 5 | 5 |  | 2 |

Example 15b

Post-Emergence Herbicidal Activity

Seeds of a variety of test species were sown in standard soil in pots. After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table 3.

TABLE 3

Application post-emergence

| Example number | Rate (g/Ha) | SETFA | ABUTH | AMARE | ALOMY | ECHCG | ZEAMX |
|---|---|---|---|---|---|---|---|
| A1 | 1000 | 5 | 5 | 5 | 5 | 5 | 5 |
| A2 | 1000 | 5 | 5 | 5 | 5 | 5 | 3 |
| A3 | 1000 | 5 | 5 | 5 | 5 | 5 | 3 |
| A4 | 1000 | 4 | 4 | 5 | 4 | 2 | 1 |
| A5 | 1000 | 5 | 5 | 5 | 5 | 5 | 4 |
| A6 | 1000 | 5 | 5 | 5 | 5 | 5 | 5 |
| A7 | 1000 | 5 | 5 | 5 | 5 | 4 | 4 |
| A8 | 1000 | 5 | 5 | 5 | 5 | 5 | 4 |
| A9 | 1000 | 4 | 5 | 5 | 4 | 4 | 1 |
| A10 | 1000 | 4 | 5 | 5 | 4 | 4 | 2 |
| A11 | 1000 | 5 | 5 | 5 | 4 | 4 | 1 |
| A16 | 1000 | 5 | 5 | 5 | 3 | 5 | 4 |
| A17 | 1000 | 5 | 5 | 5 | 3 | 5 | 4 |
| A18 | 1000 | 5 | 5 | 5 | 4 | 5 | 5 |
| A19 | 1000 | 2 | 5 | 5 | 3 | 3 | 5 |
| A20 | 1000 | 5 | 5 | 5 | 4 | 5 | 4 |
| A21 | 1000 | 5 | 5 | 5 | 5 | 5 | 4 |
| A22 | 1000 | 5 | 5 | 5 | 5 | 5 | 5 |
| A23 | 1000 | 5 | 5 | 4 | 1 | 4 | 4 |
| A24 | 1000 | 5 | 5 | 5 | 4 | 5 | 5 |
| A25 | 1000 | 5 | 5 | 5 | 5 | 5 | 5 |
| A26 | 1000 | 2 | 1 | 0 | 1 | 0 | 1 |
| A27 | 1000 | 3 | 4 | 0 | 1 | 0 | 2 |
| A28 | 1000 | 0 | 0 | 0 | 0 | 0 | 0 |
| A12 | 1000 | 5 | 5 | 5 |  | 5 | 4 |
| A13 | 1000 | 5 | 5 | 5 |  | 5 | 4 |
| A29 | 1000 | 5 | 5 | 5 | 4 | 4 | 1 |
| A30 | 1000 | 4 | 5 | 5 | 4 | 3 | 1 |
| A31 | 1000 | 5 | 5 | 1 | 4 | 3 | 1 |
| A32 | 1000 | 2 | 5 | 2 | 3 | 2 | 1 |
| A33 | 1000 | 5 | 5 | 5 | 5 | 5 | 3 |

TABLE 3-continued

Application post-emergence

| Example number | Rate (g/Ha) | SETFA | ABUTH | AMARE | ALOMY | ECHCG | ZEAMX |
|---|---|---|---|---|---|---|---|
| A34 | 1000 | 3 | 5 | 2 | 3 | 0 | 2 |
| A36 | 1000 | 5 | 5 | 5 | 5 | 5 | 5 |
| A37 | 1000 | 5 | 5 | 5 |   | 5 | 4 |
| A38 | 1000 | 5 | 5 | 5 |   | 5 | 5 |
| A39 | 1000 | 5 | 5 | 5 |   | 5 | 5 |
| A40 | 1000 | 5 | 5 | 5 |   | 5 | 5 |

ABUTH = Abutilon theophrasti;; AMARE = Amaranthus retroflexus; SETFA = Setaria faberi; ALOMY = Alopecurus myosuroides; ECHCG = Echinochloa crus-galli; ZEAMX = Zea mays.

The invention claimed is:

1. A herbicidal compound of formula (I)

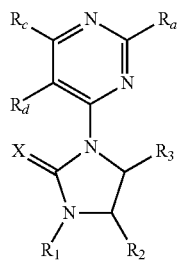

wherein

X is selected from S and O;

$R^a$ is selected from hydrogen and halogen;

$R^c$ is selected from hydrogen, formyl, hydroxyl, halogen, nitro, cyano, $C_1$-$C_8$ alkyl, $C_1$-$C_6$ cyanoalkyl, $C_1$-$C_6$ haloalkyl, $C_1$-$C_6$ hydroxyalkyl, $C_2$-$C_6$ alkenyloxy $C_1$-$C_6$ alkyl, $C_1$-$C_6$ alkylthio, $C_1$-$C_6$ alkoxy, $C_1$-$C_6$ alkoxy $C_1$-$C_6$ alkyl, $C_1$-$C_6$ alkthio, $C_1$-$C_6$ alkyl, $C_1$-$C_6$ cyanoalkoxy, $C_1$-$C_6$ haloalkoxy, $C_1$-$C_6$ alkoxy $C_1$-$C_6$ alkoxy, $C_2$-$C_8$ alkenyl, $C_2$-$C_8$ alkynyl, $C_2$-$C_6$ cyanoalkenyl, $C_2$-$C_6$ cyanoalkynyl, $C_2$-$C_6$ alkenyloxy, $C_2$-$C_6$ alkynyloxy, $C_2$-$C_6$ haloalkenyl, $C_2$-$C_6$ haloalkynyl, $C_2$-$C_6$ haloalkenyloxy, $C_2$-$C_6$ haloalkynyloxy, $C_1$-$C_6$ alkoxy $C_2$-$C_6$ alkenyl, $C_1$-$C_6$ alkoxy $C_2$-$C_6$ alkynyl, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylsulfonyloxy, $C_1$-$C_6$ alkylcarbonyl, $C_1$-$C_6$ haloalkylcarbonyl, $C_2$-$C_6$ alkenylcarbonyl, $C_2$-$C_6$ alkynylcarbonyl, $C_2$-$C_6$ haloalkenylcarbonyl, $C_2$-$C_6$ haloalkynylcarbonyl, tri $C_1$-$C_6$ alkylsilyl $C_2$-$C_6$ alkynyl, a group $R^5R^6N$—, a group $R^5C(O)N(R^6)$—, a group $R^5S(O_2)N(R^6)$—, a group $R^5R^6NSO_2$—, a group $R^5R^6NC(O)$ $C_1$-$C_6$ alkyl, a $C_6$-$C_{10}$ aryloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ aryl $C_1$-$C_3$ alkyl group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ benzyloxy group optionally substituted by from 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_3$-$C_6$ heterocyclyl group optionally substituted by from 1 to 3 groups independently selected from $C_1$-$C_4$ alkyl, a $C_3$-$C_6$ cycloalkyl group optionally substituted with from 1 to 3 groups independently selected from halogen, cyano, $C_1$-$C_6$ alkoxy and $C_1$-$C_6$ alkyl and a $C_3$-$C_6$ cycloalkenyl group optionally substituted with from 1 to 3 groups independently selected from halogen, cyano, $C_1$-$C_6$ alkoxy and $C_1$-$C_6$ alkyl;

$R^d$ is selected from hydrogen, halogen, cyano, $C_1$-$C_6$ alkyl and $C_1$-$C_6$ haloalkyl;

or $R^c$ and $R^d$ together with the carbon atoms to which they are attached form a 3-7 membered saturated or partially unsaturated ring optionally comprising from 1 to 3 heteroatoms independently selected from S, O and N and optionally substituted with from 1 to 3 groups independently selected from halogen, $C_1$-$C_6$ alkyl and $C_1$-$C_6$ haloalkyl;

$R^1$ is selected from hydrogen, $C_1$-$C_6$ alkyl optionally substituted with —$NR^{10}R^{11}$, $C_1$-$C_3$ haloalkyl and $C_1$-$C_6$ alkoxy; wherein $R^{10}$ and $R^{11}$ are independently selected from hydrogen, $C_1$-$C_6$ alkyl and $C_1$-$C_6$ haloalkyl;

$R^2$ is selected from hydrogen, hydroxyl, halogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ alkoxy $C_1$-$C_6$ alkyl, $C_1$-$C_6$ cyanoalkyl and the group —$NR^{12}R^{13}$, wherein $R^{12}$ and $R^{13}$ are independently selected from hydrogen and $C_1$-$C_6$ alkyl or $R^1$ and $R^2$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from hydroxyl, =O, $C_1$-$C_6$ alkyl or $C_1$-$C_6$ haloalkyl $R^3$ is selected from halogen, hydroxyl, —$NR^{14}R^{15}$, $C_1$-$C_6$ alkoxy, or any one of the following groups

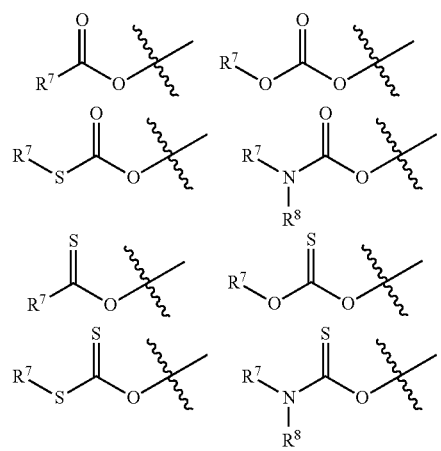

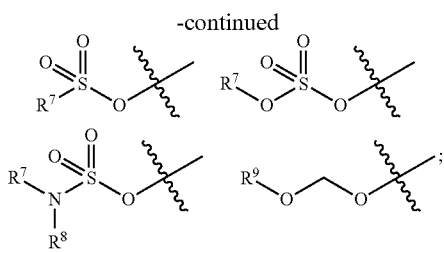

$R^5$ and $R^6$ are independently selected from hydrogen, $C_1$-$C_6$ alkyl, $C_1$-$C_6$ haloalkyl, $C_2$-$C_6$ alkenyl, $C_2$-$C_6$ alkynyl, or $R^5$ and $R^6$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen and $C_1$-$C_6$ alkyl;

$R^7$ and $R^8$ are independently selected from hydrogen, $C_1$-$C_6$ alkyl, $C_1$-$C_6$ haloalkyl, $C_2$-$C_6$ alkenyl, $C_2$-$C_6$ alkynyl, a $C_5$-$C_{10}$ heteroaryl group which can be mono- or bicyclic comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy, a $C_6$-$C_{10}$ aryl group optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, or $R^7$ and $R^8$ together with the atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;

$R^9$ is selected from $C_1$-$C_6$ alkyl or benzyl optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy;

$R^{14}$ and $R^{15}$ are independently selected from hydrogen, $C_1$-$C_{20}$ alkyl, $C_1$-$C_{20}$ haloalkyl, $C_2$-$C_{20}$ alkenyl, $C_2$-$C_{20}$ alkynyl, or $R^{14}$ and $R^{15}$ together with the carbon atoms to which they are attached form a 3-6 membered saturated or partially unsaturated ring optionally comprising from 1 to 3 heteroatoms independently selected from S, 0 and N and optionally substituted with from 1 to 3 groups independently selected from halogen and $C_1$-$C_6$ alkyl;

or an N-oxide or salt form thereof.

2. The compound of claim 1, wherein X is O.

3. The compound of claim 1, wherein $R^a$ is hydrogen.

4. The compound of claim 1, wherein $R^c$ is selected from $C_1$-$C_8$ alkyl, $C_1$-$C_6$ haloalkyl, $C_2$-$C_8$ alkenyl, $C_1$-$C_6$ cyanoalkyl, $C_1$-$C_6$ alkoxy, $C_1$-$C_6$ hydroxyalkyl, $C_1$-$C_6$ alkoxy $C_1$-$C_6$ alkyl, $C_2$-$C_6$ alkenyloxy $C_1$-$C_6$ alkyl, a group $R^5R^6NC(O)$ $C_1$-$C_6$ alkyl and $C_3$-$C_6$ cycloalkyl optionally substituted by from 1 to 3 groups independently selected from cyano, $C_1$-$C_3$ alkyl and $C_1$-$C_3$ alkoxy.

5. The compound of claim 4, wherein $R^c$ is selected from tert-butyl, (1-methyl-1-cyano)-eth-1-yl, 1,1-difluoroethyl, 1-fluoro-1-methylethyl and trifluoromethyl.

6. The compound of claim 1, wherein $R^d$ is hydrogen.

7. The compound of claim 1, wherein $R^3$ is selected from halogen, hydroxyl, —$NR^{14}R^{15}$, $C_1$-$C_6$ alkoxy, or any of the following groups

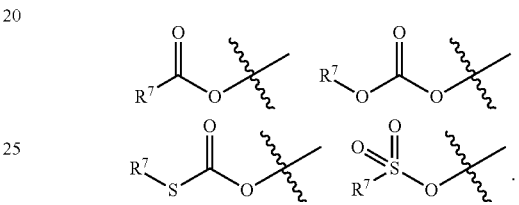

8. The compound of claim 7, wherein $R^3$ is hydroxyl.

9. The compound of claim 1, wherein $R^1$ is $C_1$-$C_3$ alkyl, $C_1$-$C_3$ alkoxy or $C_1$-$C_3$ haloalkyl.

10. The compound of claim 1, wherein $R^2$ is hydrogen, hydroxyl, $C_1$-$C_3$ alkyl, $C_1$-$C_3$ alkoxy, $C_1$-$C_3$ haloalkyl, $C_1$-$C_3$ haloalkoxy allyl.

11. A herbicidal composition comprising a compound of formula I as defined in claim 1 together with at least one agriculturally acceptable adjuvant or diluent.

12. A composition according to claim 11 which comprises a further herbicide in addition to the compound of formula I.

13. A composition according to claim 11 which comprises a safener.

14. A method of controlling weeds in crops of useful plants, the method comprising applying to said weeds, or to the locus of said weeds, or to said useful plants, or to the locus of said useful plants, a compound of formula I as defined in claim 1.

* * * * *